United States Patent
Swayze et al.

(10) Patent No.: US 9,463,022 B2
(45) Date of Patent: Oct. 11, 2016

(54) MOTOR DRIVEN ROTARY INPUT CIRCULAR STAPLER WITH LOCKABLE FLEXIBLE SHAFT

(71) Applicant: Ethicon Endo-Surgery, Inc., Cincinnati, OH (US)

(72) Inventors: Jeffrey S. Swayze, Hamilton, OH (US); Chester O. Baxter, III, Loveland, OH (US); Frederick E. Shelton, IV, Hillsboro, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 728 days.

(21) Appl. No.: 13/716,323

(22) Filed: Dec. 17, 2012

(65) Prior Publication Data

US 2014/0166718 A1 Jun. 19, 2014

(51) Int. Cl.
- *A61B 17/04* (2006.01)
- *A61B 17/10* (2006.01)
- *A61B 17/115* (2006.01)
- *A61B 17/00* (2006.01)

(52) U.S. Cl.
CPC .. *A61B 17/1155* (2013.01); *A61B 2017/00314* (2013.01); *A61B 2017/00323* (2013.01); *A61B 2017/00327* (2013.01)

(58) Field of Classification Search
CPC ................ A61B 2017/003; A61B 2017/2905; A61B 2017/2908; A61B 17/1155
USPC .......................................... 227/175.1–182.1
See application file for complete search history.

(56) References Cited

U.S. PATENT DOCUMENTS

| 4,648,733 | A | * | 3/1987 | Merkt | ..................... F16L 11/18 138/120 |
| 4,754,909 | A | * | 7/1988 | Barker | ................. A61B 17/072 227/19 |
| 4,805,823 | A | | 2/1989 | Rothfuss | |
| 4,949,927 | A | * | 8/1990 | Madocks | ............... F16M 11/40 248/160 |

(Continued)

FOREIGN PATENT DOCUMENTS

| EP | 0173451 A1 | 3/1986 |
| EP | 0634144 A1 | 1/1995 |

(Continued)

OTHER PUBLICATIONS

Non-Provisional U.S. Appl. No. 13/688,951, filed Nov. 29, 2012.

(Continued)

*Primary Examiner* — Robert Long
(74) *Attorney, Agent, or Firm* — Frost Brown Todd LLC

(57) ABSTRACT

A circular stapler apparatus and method for stapling tissue include a shaft assembly and an anvil. The anvil is configured to proximally retract toward the shaft assembly, which at least severs or staples tissue based on a single rotary input. The shaft assembly includes a plurality of joint segments, and each joint segment includes a resilient member. The plurality of joint segments are configured to pivot relative to one another in a first, uncompressed position and are configured to lock against one another to prevent pivoting in a second, compressed position. A first plurality of joint segments defines a proximal portion that is attached to a first cable or shaft. A second plurality of joint segments defines a distal portion that is selectively lockable independent of the proximal portion and that is attached to a second cable or shaft.

21 Claims, 18 Drawing Sheets

(56) References Cited

U.S. PATENT DOCUMENTS

| | | | |
|---|---|---|---|
| 5,205,459 A | 4/1993 | Brinkerhoff et al. | |
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,333,773 A | 8/1994 | Main et al. | |
| 5,348,259 A * | 9/1994 | Blanco | A61B 17/115 227/19 |
| 5,350,104 A | 9/1994 | Main et al. | |
| 5,395,030 A | 3/1995 | Kuramoto et al. | |
| 5,415,334 A | 5/1995 | Williamson, IV et al. | |
| 5,433,721 A * | 7/1995 | Hooven | A61B 17/072 227/175.1 |
| 5,465,895 A | 11/1995 | Knodel et al. | |
| 5,533,661 A | 7/1996 | Main et al. | |
| 5,597,107 A | 1/1997 | Knodel et al. | |
| 5,607,094 A * | 3/1997 | Clark | A61B 17/072 227/175.1 |
| 5,632,432 A | 5/1997 | Schulze et al. | |
| 5,673,840 A | 10/1997 | Schulze et al. | |
| 5,704,534 A | 1/1998 | Huitema et al. | |
| 5,814,055 A | 9/1998 | Knodel et al. | |
| 5,823,066 A * | 10/1998 | Huitema | A61B 17/07207 227/175.1 |
| 5,899,425 A * | 5/1999 | Corey, Jr. | A61B 17/02 248/276.1 |
| 5,916,146 A * | 6/1999 | Allotta | A61B 1/0051 600/139 |
| 6,345,793 B1 * | 2/2002 | Mauro | F16C 1/02 248/104 |
| 6,783,524 B2 | 8/2004 | Anderson et al. | |
| 6,860,668 B2 * | 3/2005 | Ibrahim | A61B 17/02 248/181.1 |
| 6,978,921 B2 | 12/2005 | Shelton, IV et al. | |
| 7,000,818 B2 | 2/2006 | Shelton, IV et al. | |
| 7,143,923 B2 | 12/2006 | Shelton, IV et al. | |
| 7,303,108 B2 | 12/2007 | Shelton, IV et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,543,730 B1 * | 6/2009 | Marczyk | A61B 17/07207 227/175.1 |
| 7,637,905 B2 * | 12/2009 | Saadat | A61B 1/0055 600/104 |
| 7,721,930 B2 | 5/2010 | McKenna et al. | |
| 7,794,475 B2 | 9/2010 | Hess et al. | |
| 7,819,884 B2 * | 10/2010 | Lee | A61B 90/36 600/114 |
| 8,568,390 B2 * | 10/2013 | Mueller | A61B 17/29 227/176.1 |
| 8,603,135 B2 * | 12/2013 | Mueller | A61B 17/29 606/170 |
| 8,696,556 B2 * | 4/2014 | Ibrahim | A61B 17/02 600/205 |
| 8,893,949 B2 | 11/2014 | Shelton et al. | |
| 9,259,240 B2 | 2/2016 | Malkowski et al. | |
| 2003/0165352 A1 * | 9/2003 | Ibrahim | A61B 17/02 403/56 |
| 2003/0216619 A1 * | 11/2003 | Scirica | A61B 17/0293 600/229 |
| 2006/0047308 A1 * | 3/2006 | Ortiz | A61B 17/07207 606/219 |
| 2007/0015965 A1 | 1/2007 | Cox et al. | |
| 2007/0106317 A1 * | 5/2007 | Shelton, IV | A61B 17/07207 606/170 |
| 2007/0135803 A1 * | 6/2007 | Belson | A61B 1/00154 606/1 |
| 2007/0282356 A1 * | 12/2007 | Sonnenschein | A61B 17/068 606/153 |
| 2009/0090764 A1 * | 4/2009 | Viola | A61B 17/07207 227/176.1 |
| 2009/0289096 A1 * | 11/2009 | Shelton, IV | A61B 17/07207 227/180.1 |
| 2010/0010512 A1 * | 1/2010 | Taylor | A61B 17/04 606/144 |
| 2010/0069715 A1 * | 3/2010 | Perry | A61B 1/0055 600/114 |
| 2010/0228191 A1 | 9/2010 | Alvarez et al. | |
| 2010/0320252 A1 * | 12/2010 | Viola | A61B 17/07207 227/176.1 |
| 2011/0082538 A1 * | 4/2011 | Dahlgren | A61B 17/00234 623/2.11 |
| 2011/0106078 A1 * | 5/2011 | Mueller | A61B 17/29 606/52 |
| 2011/0118707 A1 * | 5/2011 | Burbank | 606/1 |
| 2011/0184459 A1 * | 7/2011 | Malkowski | A61B 17/29 606/206 |
| 2012/0074201 A1 * | 3/2012 | Baxter, III | A61B 17/07207 227/180.1 |
| 2014/0005678 A1 | 1/2014 | Shelton, IV et al. | |
| 2014/0025046 A1 * | 1/2014 | Williams | A61B 17/07207 606/1 |

FOREIGN PATENT DOCUMENTS

| | | |
|---|---|---|
| EP | 0836833 A2 | 4/1998 |
| EP | 1757218 A2 | 2/2007 |
| WO | WO 97/23158 | 7/1997 |
| WO | WO 03/030830 | 4/2003 |
| WO | WO 2010/030434 | 3/2010 |

OTHER PUBLICATIONS

Non-Provisional U.S. Appl. No. 13/688,992, filed Nov. 29, 2012.
Non-Provisional U.S. Appl. No. 13/693,430, filed Dec. 4, 2012.
Non-Provisional U.S. Appl. No. 13/693,455, filed Dec. 4, 2012.
Non-Provisional U.S. Appl. No. 13/706,827, filed Dec. 6, 2012.
Non-Provisional U.S. Appl. No. 13/716,308, filed Dec. 17, 2012.
Non-Provisional U.S. Appl. No. 13/716,313, filed Dec. 17, 2012.
Non-Provisional U.S. Appl. No. 13/716,318, filed Dec. 17, 2012.
International Search Report and Written Opinion dated Oct. 30, 2014 for Application No. PCT/US2013/075246, 19 pages.

* cited by examiner

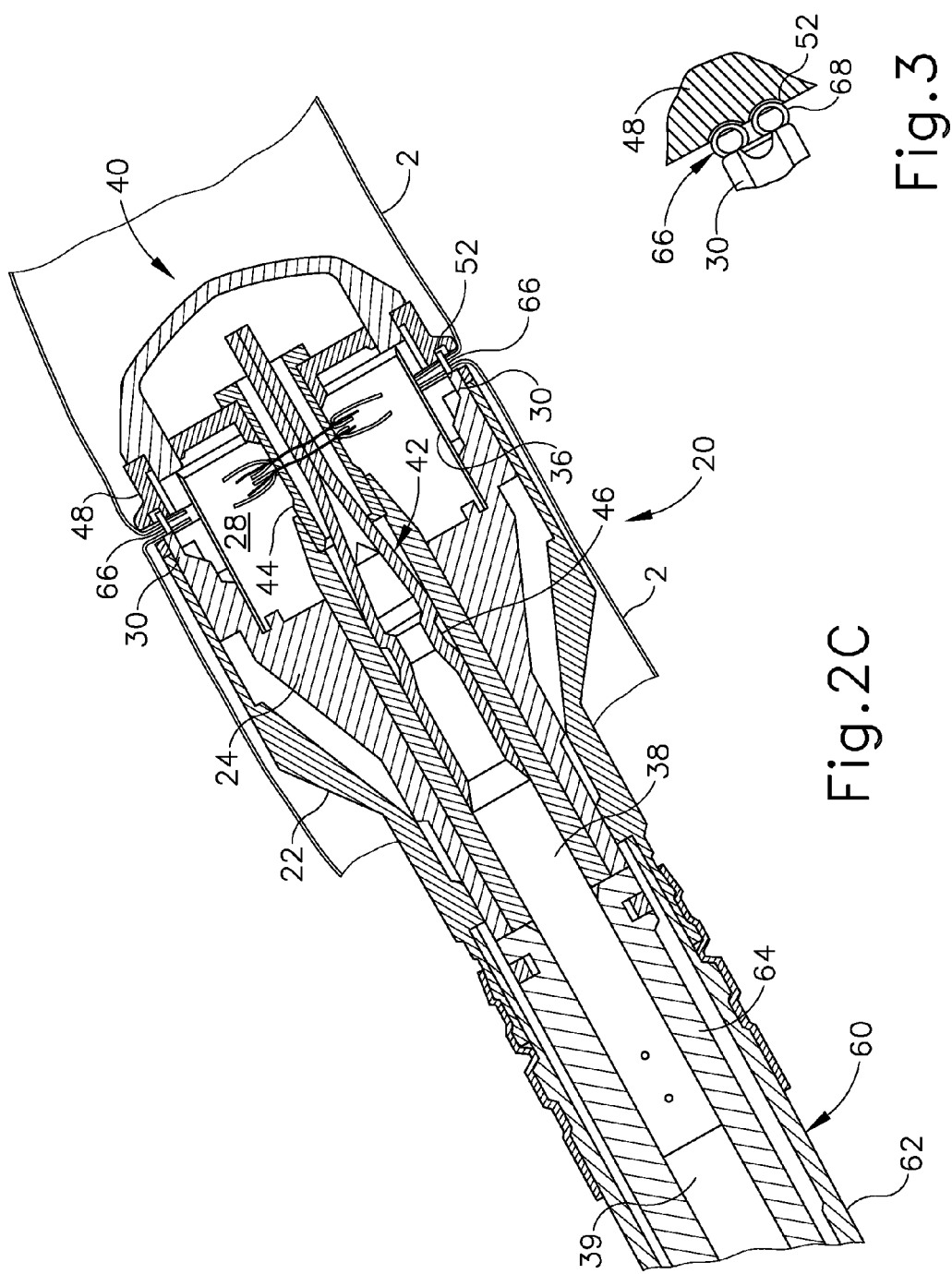

MOTOR DRIVEN ROTARY INPUT CIRCULAR STAPLER WITH LOCKABLE FLEXIBLE SHAFT

BACKGROUND

In some settings, a surgeon may want to position a surgical instrument through an orifice of the patient and use the instrument to adjust, position, attach, and/or otherwise interact with tissue within the patient. For instance, in some surgical procedures, portions of the gastrointestinal tract may be cut and removed to eliminate undesirable tissue or for other reasons. Once the desired tissue is removed, the remaining portions may need to be recoupled together. One such tool for accomplishing these anastomotic procedures is a circular stapler that is inserted through a patient's orifice.

Examples of circular surgical staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996. The disclosure of each of the above-cited U.S. patents is incorporated by reference herein. Some such staplers are operable to clamp down on layers of tissue, cut through the clamped layers of tissue, and drive staples through the layers of tissue to substantially seal the severed layers of tissue together near the severed ends of the tissue layers, thereby joining two severed ends of an anatomical lumen.

Merely additional other exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; and U.S. Pat. No. 7,721,930, entitled "Disposable Cartridge with Adhesive for Use with a Stapling Device," issued May 25, 2010. The disclosure of each of the above-cited U.S. patents is incorporated by reference herein. While the surgical staplers referred to above are described as being used in endoscopic procedures, it should be understood that such surgical staplers may also be used in open procedures and/or other non-endoscopic procedures.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 2C depicts an enlarged longitudinal cross-sectional view of the stapling head assembly of FIG. 2A showing an exemplary staple driver and blade in a fired position;

FIG. 3 depicts an enlarged partial cross-sectional view of an exemplary staple formed against the anvil;

Figure 6:
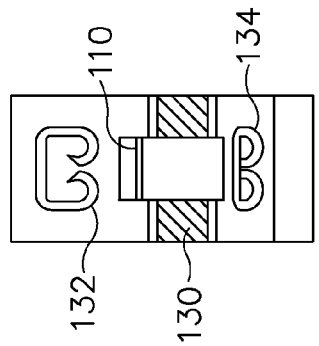
FIG. 6 depicts an diagrammatic view of the indicator window of FIG. 5 showing an exemplary indicator bar and exemplary corresponding staple representations.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

FIGS. 1-6 depict an exemplary circular surgical stapling instrument (10) having a stapling head assembly (20), a shaft assembly (60), and an actuator handle assembly (70), each of which will be described in more detail below. Shaft assembly (60) extends distally from actuator handle assembly (70) and stapling head assembly (20) is coupled to a distal end of shaft assembly (60). In brief, actuator handle assembly (70) is operable to actuate a staple driver (24) of stapling head assembly (20) to drive a plurality of staples (66) out of stapling head assembly (20). Staples (66) are bent to form completed staples by an anvil (40) that is attached at the distal end of instrument (10). Accordingly, tissue (2), shown in FIGS. 2A-2C, may be stapled utilizing instrument (10).

In the present example, instrument (10) comprises a closure system and a firing system. The closure system comprises a trocar (38), a trocar actuator (39), and a rotating knob (98). An anvil (40) may be coupled to a distal end of trocar (38). Rotating knob (98) is operable to longitudinally translate trocar (38) relative to stapling head assembly (20), thereby translating anvil (40) when anvil (40) is coupled to trocar (38), to clamp tissue between anvil (40) and stapling head assembly (20). The firing system comprises a trigger (74), a trigger actuation assembly (84), a driver actuator (64), and a staple driver (24). Staple driver (24) includes a knife (36) configured to sever tissue when staple driver (24) is actuated longitudinally. In addition, staples (66) are positioned distal to a plurality of staple driving members (30) of staple driver (24) such that staple driver (24) also drives staples (66) distally when staple driver (24) is actuated longitudinally. Thus, when trigger (74) is actuated and trigger actuation assembly (84) actuates staple driver (24) via driver actuator (64), knife (36) and members (30) substantially simultaneously sever tissue (2) and drive staples (66) distally relative to stapling head assembly (20) into tissue. The components and functionalities of the closure system and firing system will now be described in greater detail.

A. Exemplary Anvil

Figure 1:
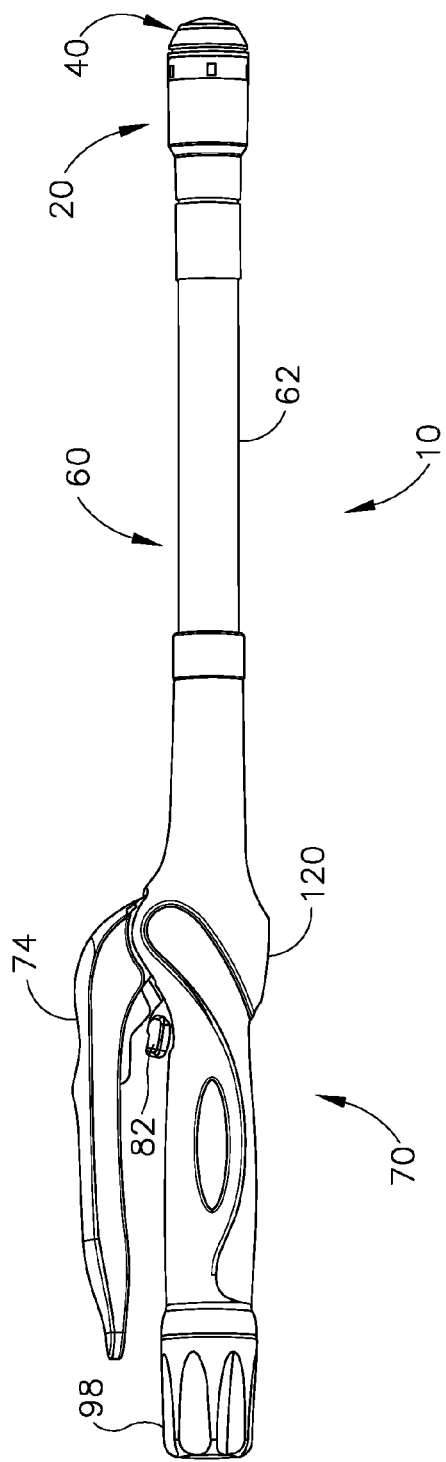
FIG. 1 depicts a side elevation view of an exemplary circular stapling surgical instrument.
Figure 2A:
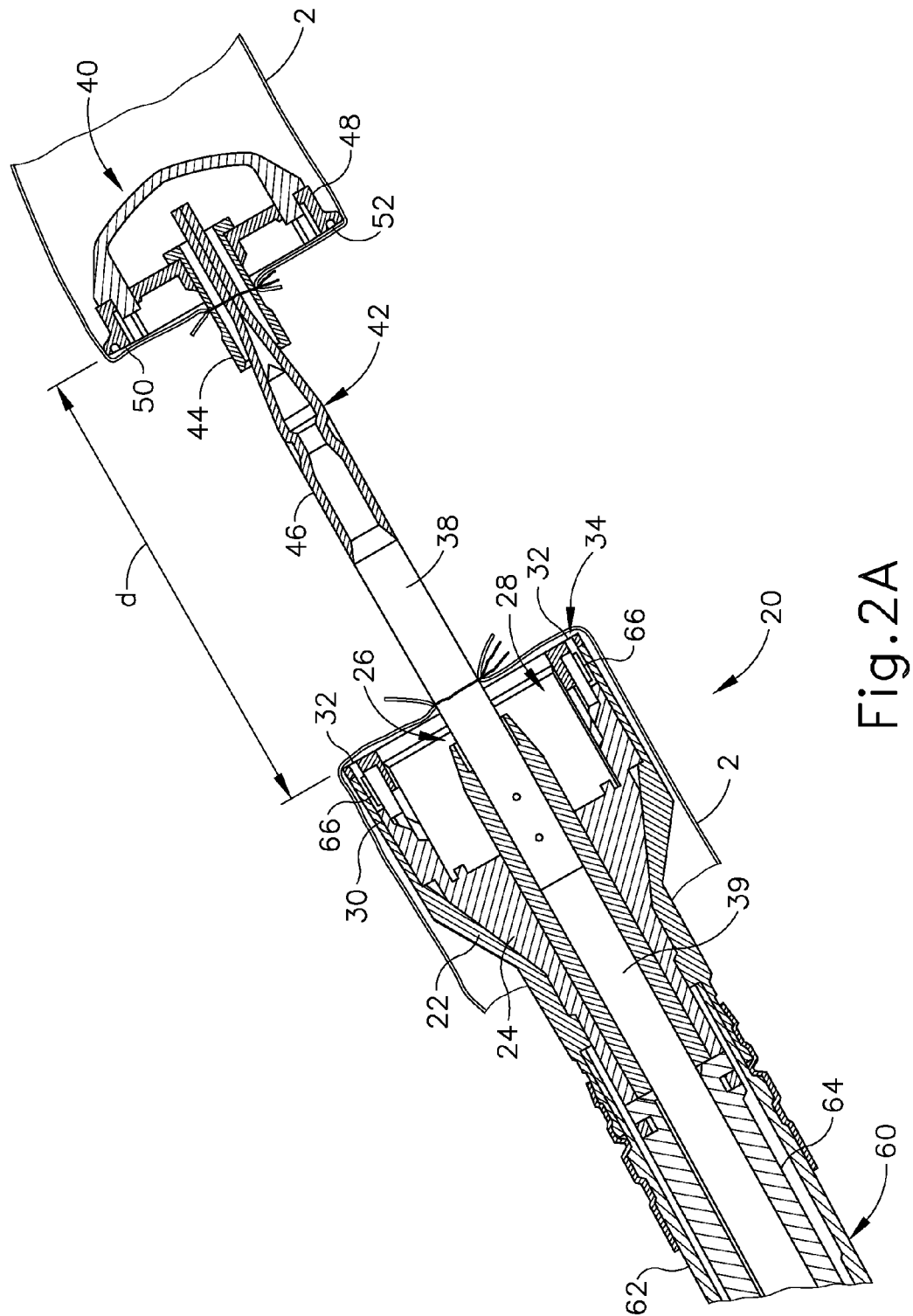
FIG. 2A depicts an enlarged longitudinal cross-section view of an exemplary stapling head assembly of the instrument of FIG. 1 showing an exemplary anvil in an open position.
Figure 2B:
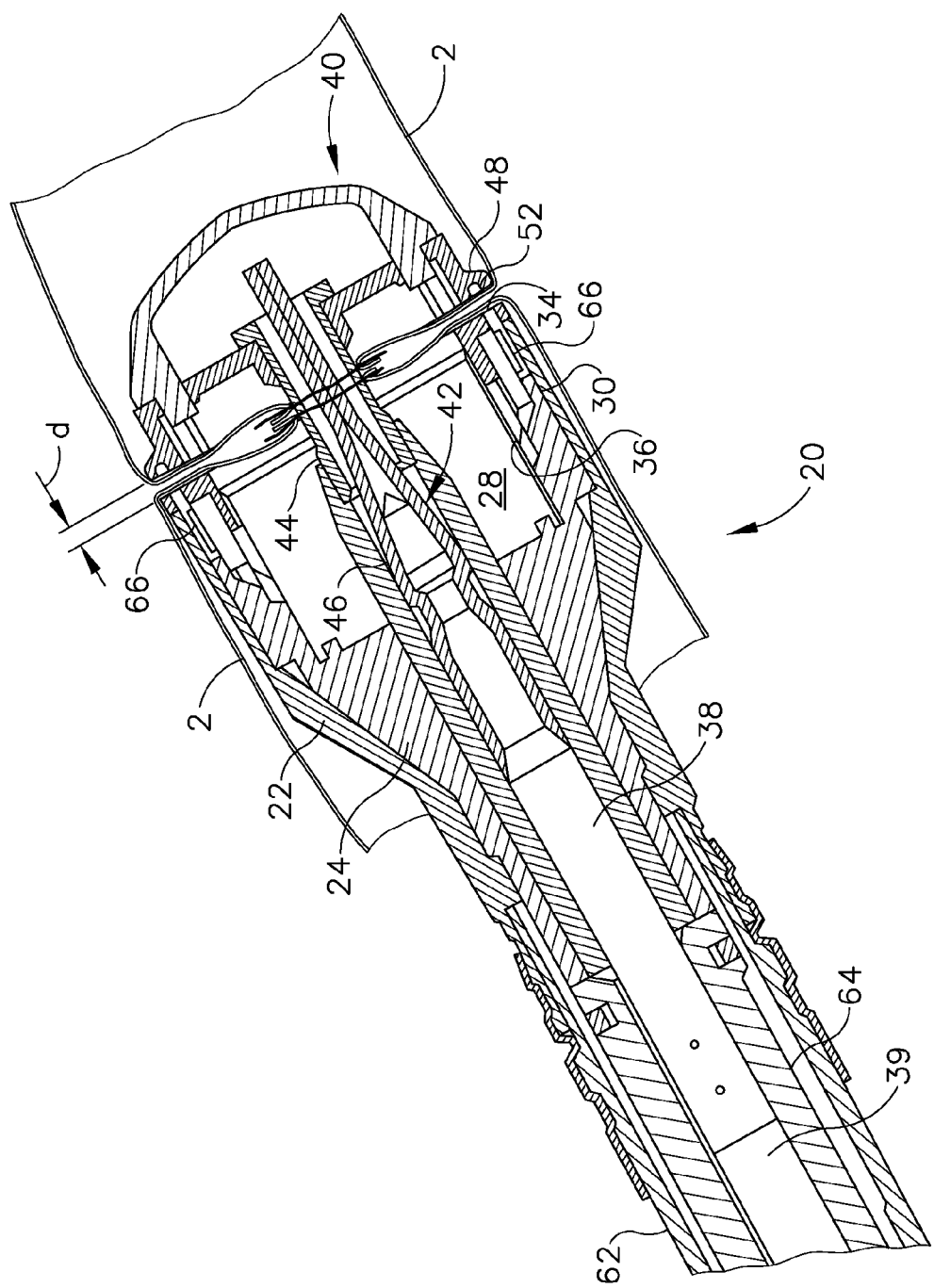
FIG. 2B depicts an enlarged longitudinal cross-sectional view of the stapling head assembly of FIG. 2A showing the anvil in a closed position.

As shown in FIGS. 1-2C, anvil (40) is selectively coupleable to instrument (10) to provide a surface against which staples (66) may be bent to staple material contained between stapling head assembly (20) and anvil (40). Anvil (40) of the present example is selectively coupleable to a trocar or pointed rod (38) that extends distally relative to stapling head assembly (20). Referring to FIGS. 2A-2C, anvil (40) is selectively coupleable via the coupling of a proximal shaft (42) of anvil (40) to a distal tip of trocar (38). Anvil (40) comprises a generally circular anvil head (48) and a proximal shaft (42) extending proximally from anvil head (48). In the example shown, proximal shaft (42) comprises a tubular member (44) having resiliently biased retaining clips (46) to selectively couple anvil (40) to trocar (38), though this is merely optional, and it should be understood that other retention features for coupling anvil (40) to trocar (38) may be used as well. For example, C-clips, clamps, threading, pins, adhesives, etc. may be employed to couple anvil (40) to trocar (38). In addition, while anvil (40) is described as selectively coupleable to trocar (38), in some versions proximal shaft (42) may include a one-way coupling feature such that anvil (40) cannot be removed from trocar (38) once anvil (40) is attached. Merely exemplary one-way features include barbs, one way snaps, collets, collars, tabs, bands, etc. Of course still other configurations for coupling anvil (40) to trocar (38) will be apparent to one of ordinary skill in the art in view of the teachings herein. For instance, trocar (38) may instead be a hollow shaft and proximal shaft (42) may comprise a sharpened rod that is insertable into the hollow shaft.

Anvil head (48) of the present example comprises a plurality of staple forming pockets (52) formed in a proximal face (50) of anvil head (48). Accordingly, when anvil (40) is in the closed position and staples (66) are driven out of stapling head assembly (20) into staple forming pockets (52), as shown in FIG. 2C, legs (68) of staples (66) are bent to form completed staples. It should be understood that staple forming pockets (52) are merely optional and may be omitted in some versions.

With anvil (40) as a separate component, it should be understood that anvil (40) may be inserted and secured to a portion of tissue (2) prior to being coupled to stapling head assembly (20). By way of example only, anvil (40) may be inserted into and secured to a first tubular portion of tissue (2) while instrument (10) is inserted into and secured to a second tubular portion of tissue (2). For instance, the first tubular portion of tissue (2) may be sutured to or about a portion of anvil (40), and the second tubular portion of tissue (2) may be sutured to or about trocar (38).

As shown in FIG. 2A, anvil (40) is then coupled to trocar (38). Trocar (38) of the present example is shown in a distal most actuated position. Such an extended position for trocar (38) may provide a larger area to which tissue (2) may be coupled prior to attachment of anvil (40). In addition, the extended position of trocar (38) may also provide for easier attachment of anvil (40) to trocar (38). Trocar (38) further includes a tapered distal tip. Such a tip may be capable of piercing through tissue and/or aiding the insertion of anvil (40) on to trocar (38), though the tapered distal tip is merely optional. For instance, in other versions trocar (38) may have a blunt tip. In addition, or in the alternative, trocar (38) may include a magnetic portion (not shown) which may attract anvil (40) towards trocar (38). Of course still further configurations and arrangements for anvil (40) and trocar (38) will be apparent to one of ordinary skill in the art in view of the teachings herein.

When anvil (40) is coupled to trocar (38), the distance between a proximal face of the anvil (40) and a distal face of stapling head assembly (20) defines a gap distance d. Trocar (38) of the present example is translatable longitudinally relative to stapling head assembly (20) via an adjusting knob (98) located at a proximal end of actuator handle assembly (70), as will be described in greater detail below. Accordingly, when anvil (40) is coupled to trocar (38), rotation of adjusting knob (98) enlarges or reduces gap distance d by actuating anvil (40) relative to stapling head assembly (20). For instance, as shown sequentially in FIGS. 2A-2B, anvil (40) is shown actuating proximally relative to actuator handle assembly (70) from an initial, open position to a closed position, thereby reducing the gap distance d and the distance between the two portions of tissue (2) to be joined. Once the gap distance d is brought within a predetermined range, stapling head assembly (20) may be fired, as shown in FIG. 2C, to staple and sever tissue (2) between anvil (40) and stapling head assembly (20). Stapling head assembly (20) is operable to staple and sever tissue (2) by a user pivoting a trigger (74) of actuator handle assembly (70), as will be described in greater detail below.

Figure 5:
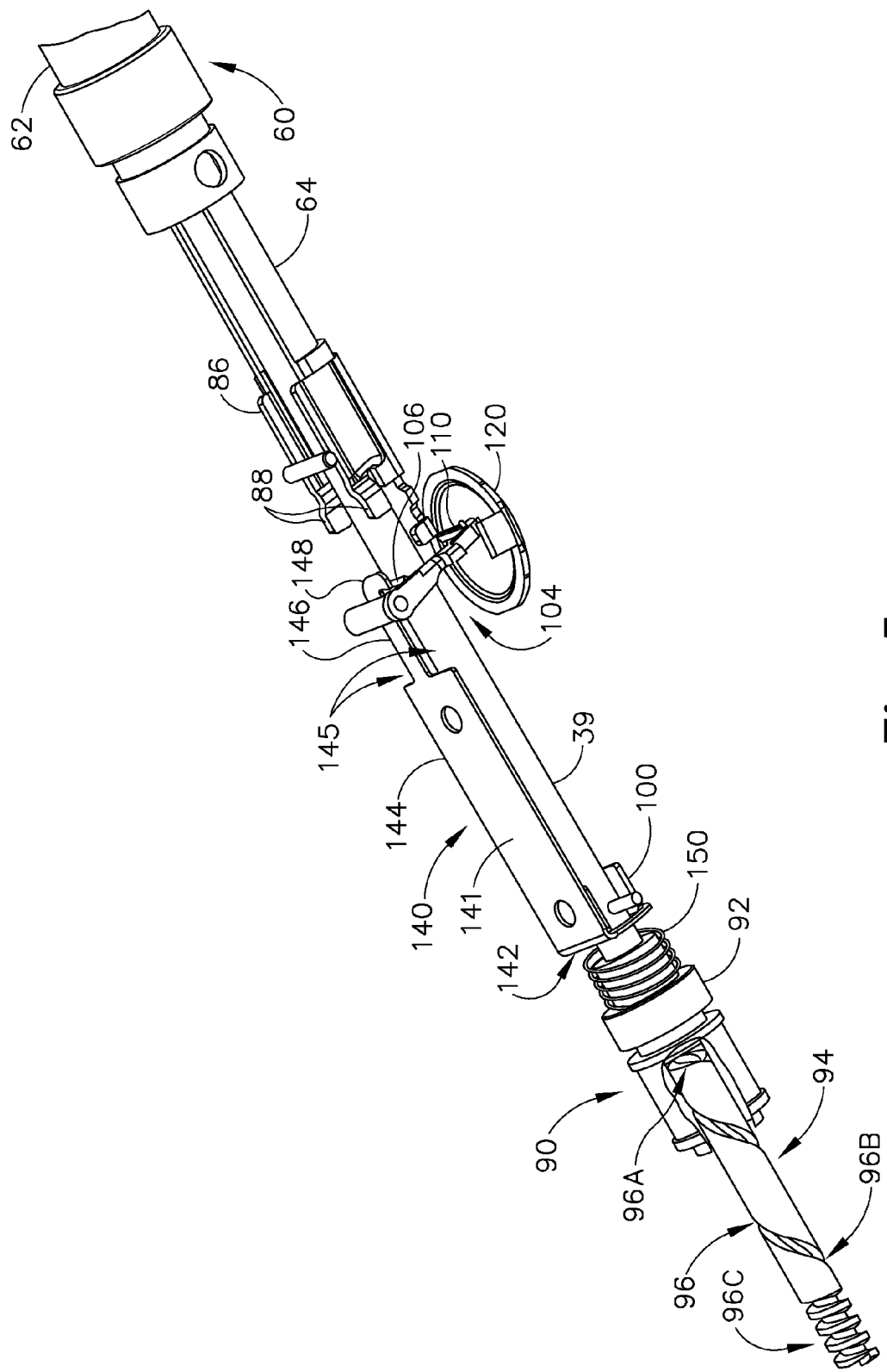
FIG. 5 depicts an enlarged partial perspective view of an exemplary indicator assembly of the surgical instrument of FIG. 1 showing an indicator window and indicator lever.

As noted above, gap distance d corresponds to the distance between anvil (40) and stapling head assembly (20). When instrument (10) is inserted into a patient, this gap distance d may not be easily viewable. Accordingly, a moveable indicator bar (110), shown in FIGS. 5-6, is provided to be visible through an indicator window (120) positioned opposite to trigger (74). Indicator bar (110) is operable to move in response to rotation of adjusting knob (98) such that the position of indicator bar (110) is representative of the gap distance d. As shown in FIG. 6, indicator window (120) further comprises a scale (130) which indicates that the anvil gap is within a desired operating range (e.g., a green colored region or "green zone") and a corresponding staple compression representation at each end of scale (130). By way of example only, as shown in FIG. 6, a first staple image (132) depicts a large staple height while a second staple image (134) depicts a small staple height. Accordingly, a user can view the position of the coupled anvil (40) relative to the stapling head assembly (20) via indicator bar (110) and scale (130). The user may then adjust the positioning of anvil (40) via adjusting knob (98) accordingly.

Referring back to FIGS. 2A-2C, a user sutures a portion of tissue (2) about tubular member (44) such that anvil head (48) is located within a portion of the tissue (2) to be stapled. When tissue (2) is attached to anvil (40), retaining clips (46) and a portion of tubular member (44) protrude out from tissue (2) such that the user may couple anvil (40) to trocar (38). With tissue (2) coupled to trocar (38) and/or another portion of stapling head assembly (20), the user attaches anvil (40) to trocar (38) and actuates anvil (40) proximally towards stapling head assembly (20) to reduce the gap distance d. Once instrument (10) is within the operating range, the user then staples together the ends of tissue (2), thereby forming a substantially contiguous tubular portion of tissue (2).

Anvil (40) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

B. Exemplary Stapling Head Assembly

Stapling head assembly (20) of the present example is coupled to a distal end of shaft assembly (60) and comprises a tubular casing (22) housing a slidable staple driver (24) and a plurality of staples (66) contained within staple pockets (32). Staples (66) and staple pockets (32) are disposed in a circular array about tubular casing (22). In the present example, staples (66) and staple pockets (32) are disposed in a pair of concentric annular rows of staples (66) and staple pockets (32). Staple driver (24) is operable to actuate longitudinally within tubular casing (22) in response to rotation of trigger (74) of actuator handle assembly (70). As shown in FIGS. 2A-2C, staple driver (24) comprises a flared cylindrical member having a trocar opening (26), a central recess (28), and a plurality of members (30) disposed circumferentially about central recess (28) and extending distally relative to shaft assembly (60). Each member (30) is configured to contact and engage a corresponding staple (66) of the plurality of staples (66) within staple pockets (32). Accordingly, when staple driver (24) is actuated distally relative to actuator handle assembly (70), each member (30) drives a corresponding staple (66) out of its staple pocket (32) through a staple aperture (34) formed in a distal end of tubular casing (22). Because each member (30) extends from staple driver (24), the plurality of staples (66) are driven out of stapling head assembly (20) at substantially the same time. When anvil (40) is in the closed position, staples (66) are driven into staple forming pockets (52) to bend legs (68) of the staples (66), thereby stapling the material located between anvil (40) and stapling head assembly (20). FIG. 3 depicts one merely exemplary staple (66) driven by a member (30) into a staple forming pocket (32) of anvil (40) to bend legs (68).

Staple driver (24) further includes a cylindrical knife (36) that is coaxial to trocar opening (26) and inset from staple pockets (32). In the present example, cylindrical knife (36) is disposed within central recess (28) to translate distally with staple driver (24). When anvil (40) is secured to trocar (38), as described above, anvil head (48) provides a surface against which cylindrical knife (36) cuts the material contained between anvil (40) and stapling head assembly (20). In some versions, anvil head (48) may include a recess (not shown) for cylindrical knife (36) to aid in cutting the material (e.g., by providing a cooperative shearing edge). In addition, or in the alternative, anvil head (48) may include one or more opposing cylindrical knives (not shown) offset from cylindrical knife (36) such that a scissor-type cutting action may be provided. Still other configurations will be apparent to one of ordinary skill in the art in view of the teachings herein. Stapling head assembly (20) is thus operable to both staple and cut tissue (2) substantially simultaneously in response to actuation by actuator handle assembly (70).

Of course stapling head assembly (20) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

As noted previously, staple driver (24) includes a trocar opening (26). Trocar opening (26) is configured to permit trocar (38) to longitudinally slide relative to stapling head assembly (20) and/or shaft assembly (60). As shown in FIGS. 2A-2C, trocar (38) is coupled to a trocar actuator (39) such that trocar (38) can be actuated longitudinally via rotation of rotating knob (98), as will be described in greater detail below in reference to actuator handle assembly (70). In the present example, trocar actuator (39) comprises an elongated, relatively stiff shaft coupled to trocar (38), though this is merely optional. In some versions, actuator (39) may comprise a longitudinally stiff material while permitting lateral bending such that portions of instrument (10) may be selectively bent or curved during use; or instrument (10) may include a preset bent shaft assembly (60). One merely exemplary material is nitinol. When anvil (40) is coupled to trocar (38), trocar (38) and anvil (40) are translatable via actuator (39) to adjust the gap distance d between anvil (40) and stapling head assembly (20). Still further configurations for actuator (39) to longitudinally actuate trocar (38) will be apparent to one of ordinary skill in the art in view of the teachings herein.

C. Exemplary Shaft Assembly

Stapling head assembly (20) and trocar (38) are positioned at a distal end of shaft assembly (60), as shown in FIGS. 2A-2C. Shaft assembly (60) of the present example comprises an outer tubular member (62) and a driver actuator (64). Outer tubular member (62) is coupled to tubular casing (22) of stapling head assembly (20) and to a body (72) of actuator handle assembly (70), thereby providing a mechanical ground for the actuating components therein. The proximal end of driver actuator (64) is coupled to a trigger actuation assembly (84) of actuator handle assembly (70), described below. The distal end of driver actuator (64) is coupled to staple driver (24) such that the rotation of trigger (74) longitudinally actuates staple driver (24). As shown in FIGS. 2A-2C, driver actuator (64) comprises a tubular member having an open longitudinal axis such that actuator (39) coupled to trocar (38) may actuate longitudinally within and relative to driver actuator (64). Of course it should be understood that other components may be disposed within driver actuator (64) as will be apparent to one of ordinary skill in the art in view of the teachings herein.

Shaft assembly (60) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

D. Exemplary Actuator Handle Assembly

Figure 4A:
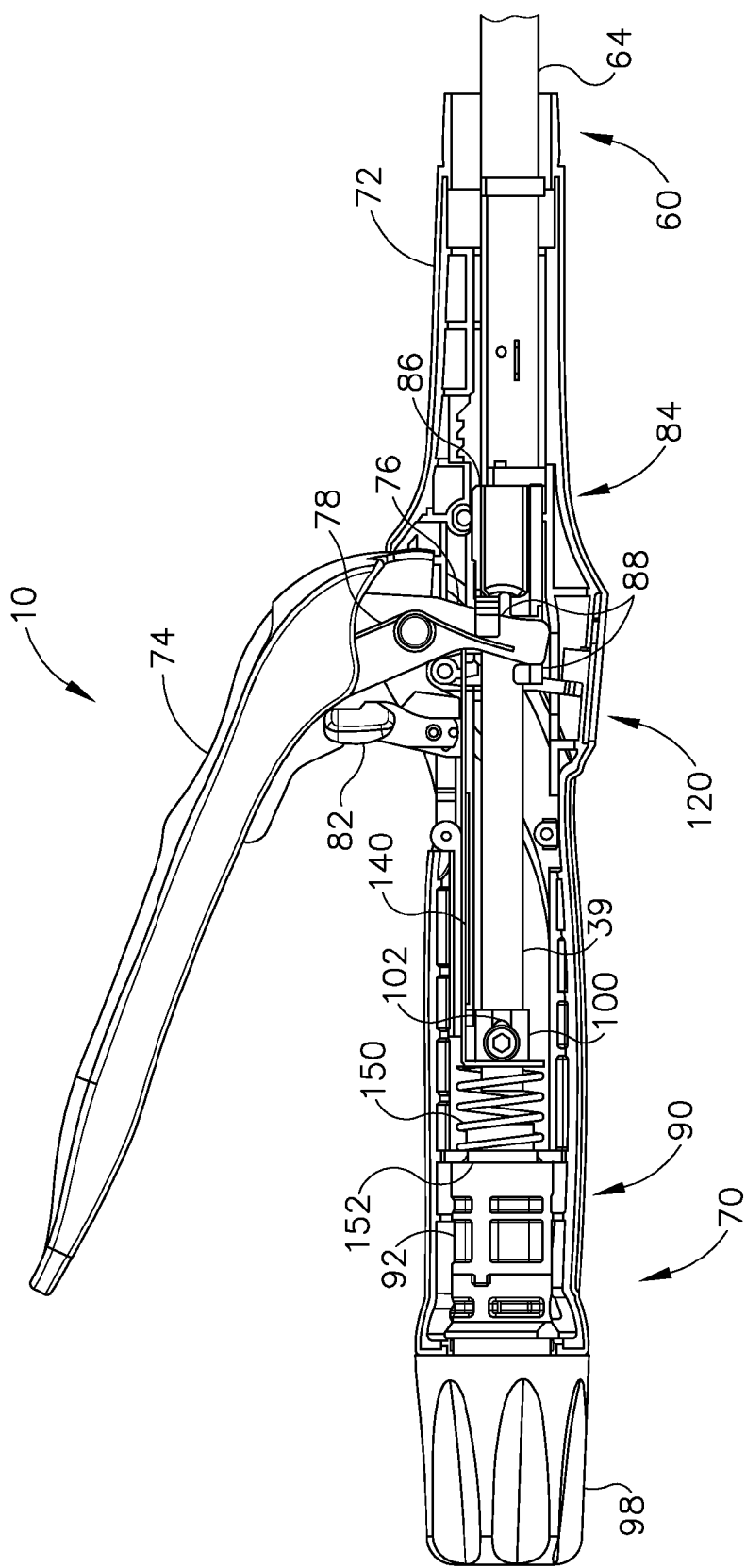
FIG. 4A depicts an enlarged side elevation view of an exemplary actuator handle assembly of the surgical instrument of FIG. 1 with a portion of the body removed, showing a trigger in an unfired position and a lockout feature in a locked position.
Figure 4B:
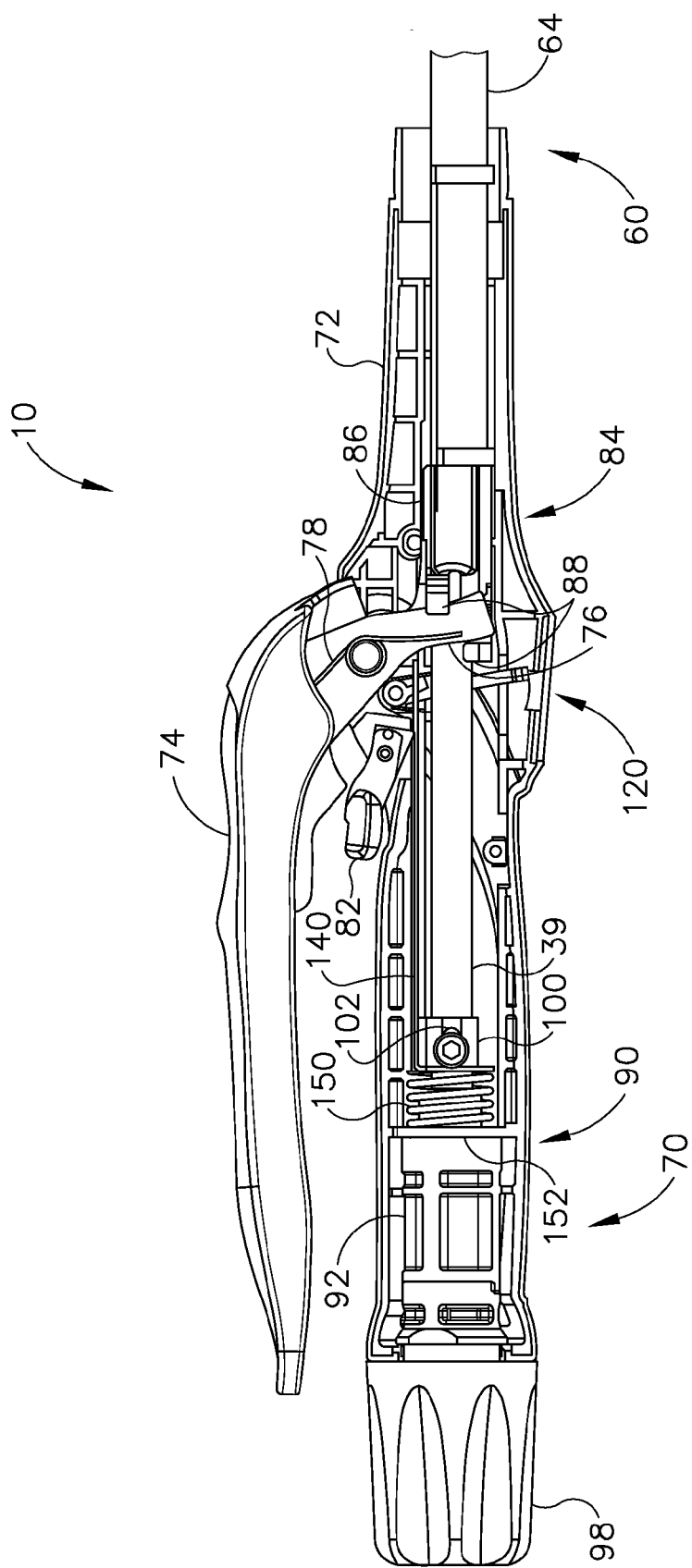
FIG. 4B depicts an enlarged side elevation view of the actuator handle assembly of FIG. 4A, showing the trigger in a fired position and the lockout feature in an unlocked position.

Referring now to FIGS. 4A-5, actuator handle assembly (70) comprises a body (72), a trigger (74), a lockout feature (82), a trigger actuation assembly (84), and a trocar actuation assembly (90). Trigger (74) of the present example is pivotably mounted to body (72) and is coupled to trigger actuation assembly (84) such that rotation of trigger (74) from an unfired position (shown in FIG. 4A) to a fired position (shown in FIG. 4B) actuates driver actuator (64) described above. A spring (78) is coupled to body (72) and trigger (74) to bias trigger (74) towards the unfired position. Lockout feature (82) is a pivotable member that is coupled to body (72). In a first, locked position, lockout feature (82) is pivoted upwards and away from body (72) such that lockout feature (82) engages trigger (74) and mechanically resists actuation of trigger (74) by a user. In a second, unlocked position, such as that shown in FIGS. 1 and 4B, lockout feature (82) is pivoted downward such that trigger (74) may be actuated by the user. Accordingly, with lockout feature (82) in the second position, trigger (74) can engage a trigger actuation assembly (84) to fire instrument (10).

As shown in FIGS. 4A-4B, trigger actuation assembly (84) of the present example comprises a slidable trigger carriage (86) engaged with a proximal end of driver actuator (64). Carriage (86) includes a set of tabs (88) on a proximal end of carriage (86) to retain and engage a pair of trigger arms (76) extending from trigger (74). Accordingly, when trigger (74) is pivoted, carriage (86) is actuated longitudinally and transfers the longitudinal motion to driver actuator (64). In the example shown, carriage (86) is fixedly coupled to the proximal end of driver actuator (64), though this is merely optional. Indeed, in one merely exemplary alternative, carriage (86) may simply abut driver actuator (64) while a distal spring (not shown) biases driver actuator (64) proximally relative to actuator handle assembly (70).

Trigger actuation assembly (84) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

Body (72) also houses a trocar actuation assembly (90) configured to actuate trocar (38) longitudinally in response to rotation of adjusting knob (98). As best shown in FIGS. 4A-5, trocar actuation assembly (90) of the present example comprises adjusting knob (98), a grooved shank (94), and a sleeve (92). Grooved shank (94) of the present example is located at a distal end of trocar actuator (39), though it should be understood that grooved shank (94) and trocar actuator (39) may alternatively be separate components that engage to transmit longitudinal movement. Adjusting knob (98) is rotatably supported by the proximal end of body (72) and is operable to rotate sleeve (92) that is engaged with grooved shank (94) via an internal tab (not shown). Grooved shank (94) of the present example comprises a continuous groove (96) formed in the outer surface of grooved shank (94). Accordingly, when adjusting knob (98) is rotated, the internal tab rides within groove (96) and grooved shank (94) is longitudinally actuated relative to sleeve (92). Since grooved shank (94) is located at the distal end of trocar actuator (39), rotating adjusting knob (98) in a first direction advances trocar actuator (39) distally relative to actuator handle assembly (70). Accordingly, the gap distance d between anvil (40) and stapling head assembly (20) is increased. By rotating adjusting knob (98) in the opposite direction, trocar actuator (39) is actuated proximally relative to actuator handle assembly (70) to reduce the gap distance d between anvil (40) and stapling head assembly (20). Thus, trocar actuation assembly (90) is operable to actuate trocar (38) in response to rotating adjustment knob (98). Of course other configurations for trocar actuation assembly (90) will be apparent to one of ordinary skill in the art in view of the teachings herein.

Groove (96) of the present example comprises a plurality of different portions (96A, 96B, 96C) that have a varying pitch or number of grooves per axial distance. The present groove (96) is divided into a distal portion (96A), a middle portion (96B) and a proximal portion (96C). As shown in FIG. 5, distal portion (96A) comprises a fine pitch or a high number of grooves over a short axial distance of grooved shank (94) such that a large number of rotations of adjusting knob (98) are required to traverse the short axial distance. Middle portion (96B) comprises a section with comparably coarser pitch or fewer grooves per axial distance such that relatively few rotations are required to traverse a long axial distance. Accordingly, the gap distance d may be quickly reduced through relatively few rotations of adjusting knob (98). Proximal portion (96C) of the present example is substantially similar to distal portion (96A) and comprises a fine pitch or a high number of grooves over a short axial distance of grooved shank (94) such that a large number of rotations are required to traverse the short axial distance. Proximal portion (96C) of the present example is positioned within sleeve (92) when anvil (40) is substantially near to stapling head assembly (20) such that indicator bar (110) moves within indicator window (120) along scale (130) to indicate that the anvil gap is within a desired operating range, as will be described in more detail below. Accordingly, when the tab is within proximal portion (96C) of groove (96), each rotation of adjusting knob (98) may reduce the gap distance d by a small amount to provide for fine tuning.

Trocar actuation assembly (90) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat. No. 5,533,661, the disclosures of which are incorporated by reference herein; and/or in accordance with other configurations as will be apparent to one of ordinary skill in the art in view of the teachings herein.

In the example shown in FIGS. 4A-4B, a U-shaped clip (100) is attached to an intermediate portion of trocar actuator (39) located distally of grooved shank (94). U-shaped clip (100) engages with a portion of body (72) to substantially prevent trocar actuator (39) from rotating about its axis when adjusting knob (98) is rotated. U-shaped clip (100) further includes an elongated slot (102) on each of its opposite sides for receiving an attachment member, such as a screw, bolt, pin, clip, etc., to selectively adjust the longitudinal position of elongated slot (102) of U-shaped clip (100) relative to trocar actuator (39) for purposes of calibrating indicator bar (110) relative to scale (130).

As shown in FIG. 5, actuator handle assembly (70) further includes an indicator bracket (140) configured to engage and pivot an indicator (104). Indicator bracket (140) of the present example is slidable relative to body (72) along a pair of slots formed on body (72). Indicator bracket (140) comprises a rectangular plate (144), an indicator arm (146), and an angled flange (142). Angled flange (142) is formed at the proximal end of rectangular plate (144) and includes an aperture (not shown) to slidable mount onto trocar actuator (39) and/or grooved shank (94). A coil spring (150) is interposed between flange (142) and a boss (152) to bias flange (142) against U-shaped clip (100). Accordingly, when U-shaped clip (100) actuates distally with trocar actuator (39) and/or grooved shank (94), coil spring (150) urges indicator bracket (140) to travel distally with U-shaped clip (100). In addition, U-shaped clip (100) urges indicator bracket (140) proximally relative to boss (152) when trocar actuator (39) and/or grooved shank (94) translate proximally, thereby compressing coil spring (150). Of course, it should be understood that in some versions indicator bracket (140) may be fixedly attached to trocar actuator (39) and/or grooved shank (94).

In the present example, a portion of lockout feature (82) abuts a surface (141) of indicator bracket (140) when indicator bracket (140) is in a longitudinal position that does not correspond to when the anvil gap is within a desired operating range (e.g., a green colored region or "green zone"). When the anvil gap is within a desired operating range (e.g., a green colored region or "green zone"), indicator bracket (140) narrows to provide a pair of gaps (145) on either side of an indicator arm (146) that permits lockout feature (82) to pivot, thereby releasing trigger (74). Accordingly, lockout feature (82) and indicator bracket (140) can substantially prevent a user from releasing and operating trigger (74) until anvil (40) is in a predetermined operating range. Of course it should be understood that lockout feature (82) may be omitted entirely in some versions.

This operating range may be visually communicated to the user via an indicator bar (110) of an indicator (104) shown against a scale (130), described briefly above. At the distal end of indicator bracket (140) is a distally projecting indicator arm (146) which terminates at a laterally projecting finger (148) for controlling the movement of indicator (104). Indicator arm (146) and finger (148), best shown in FIG. 5, are configured to engage a tab (106) of indicator (104) such that indicator (104) is pivoted when indicator bracket (140) is actuated longitudinally. In the present example, indicator (104) is pivotably coupled to body (72) at a first end of indicator (104), though this is merely optional and other pivot points for indicator (104) will be apparent to one of ordinary skill in the art in view of the teachings herein. An indicator bar (110) is positioned on the second end of indicator (104) such that indicator bar (110) moves in response to the actuation of indicator bracket (140). Accordingly, as discussed above, indicator bar (110) is displayed through an indicator window (120) against a scale (130) (shown in FIG. 6) to show the relative gap distance d between anvil (40) and stapling head assembly (20).

Of course indicator bracket (140), indicator (104), and/or actuator handle assembly (70) may be further constructed in accordance with at least some of the teachings of U.S. Pat. No. 5,205,459; U.S. Pat. No. 5,271,544; U.S. Pat. No. 5,275,322; U.S. Pat. No. 5,285,945; U.S. Pat. No. 5,292,053; U.S. Pat. No. 5,333,773; U.S. Pat. No. 5,350,104; U.S. Pat.

No. 5,533,661, the disclosures of which are incorporated by reference herein; and/or in accordance with other configurations as will be apparent to one of ordinary skill in the art in view of the teachings herein.

II. Exemplary Surgical Stapler with Flexible Shaft Assembly

Figure 7:
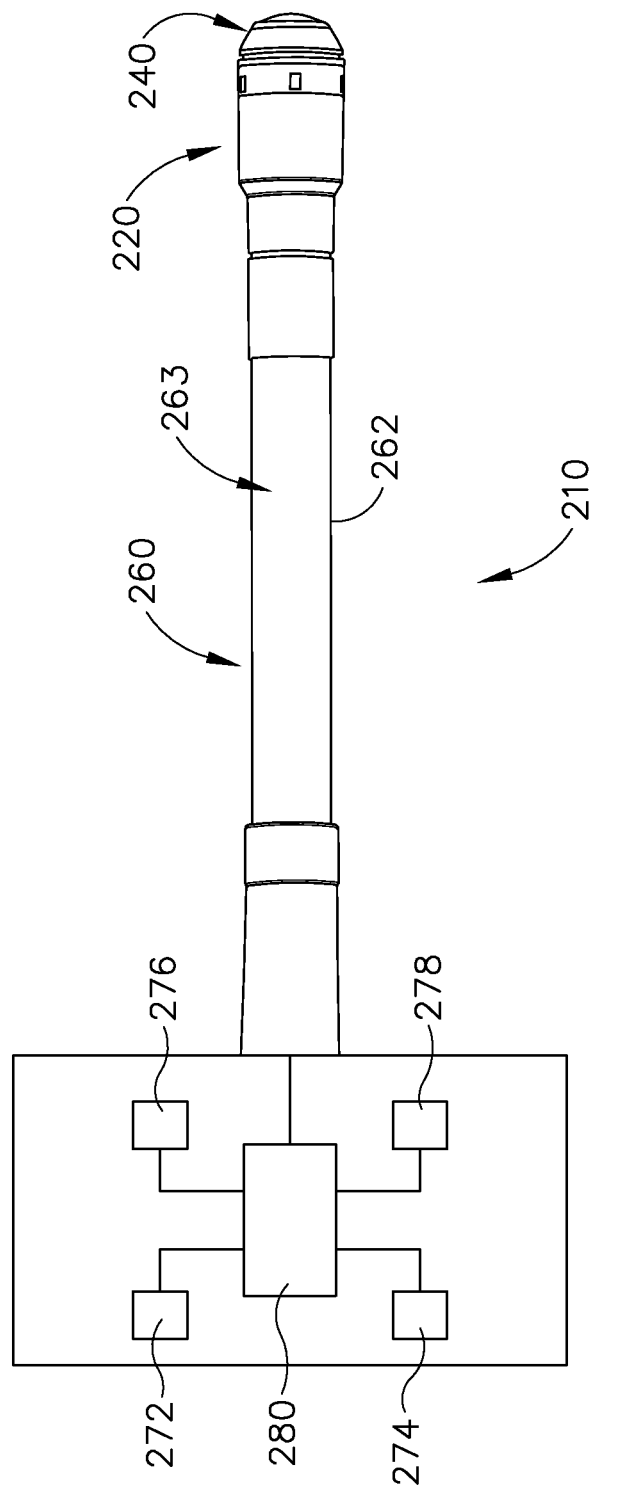
FIG. 7 depicts a side elevation and partially schematic view of an exemplary rotary driven circular stapling surgical instrument.

FIG. 7 shows an example of an instrument (210) that is similar to instrument (10) except that instrument (210) includes a stapling head assembly (220) that is able to actuate both clamping and driving (stapling and severing) features of instrument (210) based on a single rotary input. Instrument (210) includes a motorized handle assembly (270) and a shaft assembly (260) that extends distally from handle assembly (270). Shaft assembly (260) comprises outer tubular member (262) and a flexible section (263). Stapling head assembly (220) is coupled to a distal end of shaft assembly (260) and operates against anvil (240) in a manner similar to the operation of stapling head assembly (20) against anvil (40) to form tissue-capturing staples (66) as described above. Handle assembly (270) is operable to provide a single rotary output to clamp tissue between stapling head assembly (220) and anvil (240), to cut tissue (2) clamped between stapling head assembly (220) and anvil (240), and to drive staples (66) through tissue toward anvil (240). For example, handle assembly (270) is operable to actuate shaft assembly (260) to draw anvil (240) toward stapling head assembly (220) to clamp tissue between stapling head assembly (220) and anvil (240). Handle assembly (270) is further operable to actuate a staple driver of stapling head assembly (220) to drive a plurality of staples (66) out of stapling head assembly (220). Staples (66) are bent to form completed staples by anvil (240), to thereby staple tissue (2). Stapling head assembly (220) also includes a cylindrical knife, similar to cylindrical knife (36) described above, to cut tissue (2) near the staple line at substantially the same time as staples (66) are formed. By way of example only, stapling head assembly (220) may be constructed in accordance with at least some of the teachings of U.S. patent application Ser. No. 13/716,318, entitled "Motor Driven Rotary Input Circular Stapler with Modular End Effector," filed on Dec. 17, 2012, published as U.S. Pat. Pub. No 2014/0166728 on Jun. 19, 2014, the disclosure of which is incorporated by reference herein. Other suitable ways in which stapling head assembly (220) may be constructed will be apparent to those of ordinary skill in the art in view of the teachings herein.

Handle assembly (270) includes a motor (272), a power source (274), a user input (276) that is operable to actuate motor (272), a user input (278) that is operable to actuate a tension cable in shaft assembly (262), and a control module (280). Control module (280) is in communication with motor (272), power source (274), and user input (276). Control module (280) is operable to act as a controller to direct operations of instrument (210) in a manner as will be apparent to those of ordinary skill in the art in view of the teachings herein. In some versions, control module (280) is also in communication with user input (278). For instance, control module (280) may be operable to activate a motorized or otherwise powered actuator to selectively provide tension in a tension cable in response to a user actuating user input (278). In some other versions, user input (278) is purely mechanical, such that the tension of the tension cable is adjusted manually. For instance user input (278) may include a slider that pulls or releases the tension cable, a knob that drives a screw mechanism to pull or release the tension cable, or any other suitable type of manual input. Even in versions where user input (278) adjusts tension in the tension cable manually, control module (280) may still be configured to sense tension in the cable and account for such data in executing control algorithms. For instance, control module (280) may be programmed with a control logic that prevents motor (272) from being activated in the absence of tension in the tension cable, in a manner as will be apparent to one of ordinary skill in the art in view of the teachings herein.

Motor (272) is operable to provide a single rotary output to drive shaft assembly (260) and thereby drive stapling head assembly (220) as described above. Power source (274) is operable to provide power to operate motor (272). Control module (280) may read a signal transmitted by actuation of user input (276) to actuate motor (272) to thereby drive stapling head assembly (220). By way of example only, handle assembly (270) may be constructed in accordance with at least some of the teachings of U.S. patent application Ser. No. 13/716,308, entitled "Circular Stapler with Selectable Motorized and Manual Control," filed on Dec. 17, 2012 and published as U.S. Pat. Pub. No. 2014/0166727 on Jun. 19, 2014, the disclosure of which is incorporated by reference herein. As another example, handle assembly (270) may be constructed in accordance with at least some of the teachings of U.S. patent application Ser. No. 13/716,313, entitled "Circular Stapler with Selectable Motorized and Manual Control, Including a Control Ring," filed on Dec. 17, 2012 and published as U.S. Pat. Pub. No. 2014/0166717 on Jun. 19, 2014, the disclosure of which is incorporated by reference herein. Other suitable ways in which handle assembly (270) may be constructed will be apparent to those of ordinary skill in the art in view of the teachings herein.

Flexible section (263) of outer tubular member (262) is able to change from a first flexible, loose, and unlocked configuration to a second rigid and locked configuration. Flexible section (263) in the first unlocked configuration may flexibly advance or retract through a tortuous, winding pathway of a lumen of tissue such as, for example, a colon of the gastrointestinal tract, to a desired surgical location. At the desired surgical location, as described below, flexible section (263) is able to lock into the second rigid configuration prior to the actuation of stapling head assembly (220) as described above. The more rigid configuration provides a solid mechanical ground for stapling head assembly (220) relative to handle assembly (270). After stapling head assembly (220) has operated on the clamped tissue, flexible section (263) unlocks into the first unlocked configuration and is able to flexibly retract through the tissue lumen that now has portions connected at the desired surgical site by a formed anastomosis (connecting two severed tissue lumens together via, for example, staples (66)).

Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

A. Exemplary Flexible Shaft Sections

Figure 8A:
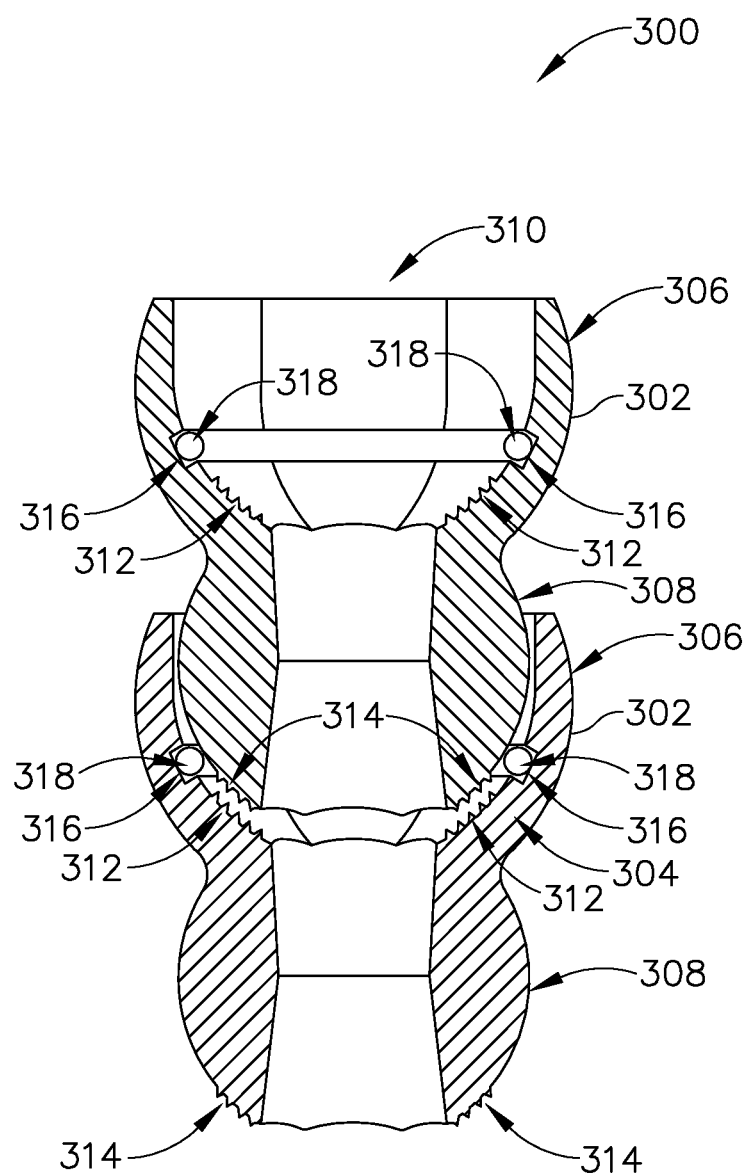
FIG. 8A depicts a cross-sectional elevation view of an exemplary shaft assembly that may be incorporated into the instrument of FIG. 7, in a first position.
Figure 8B:
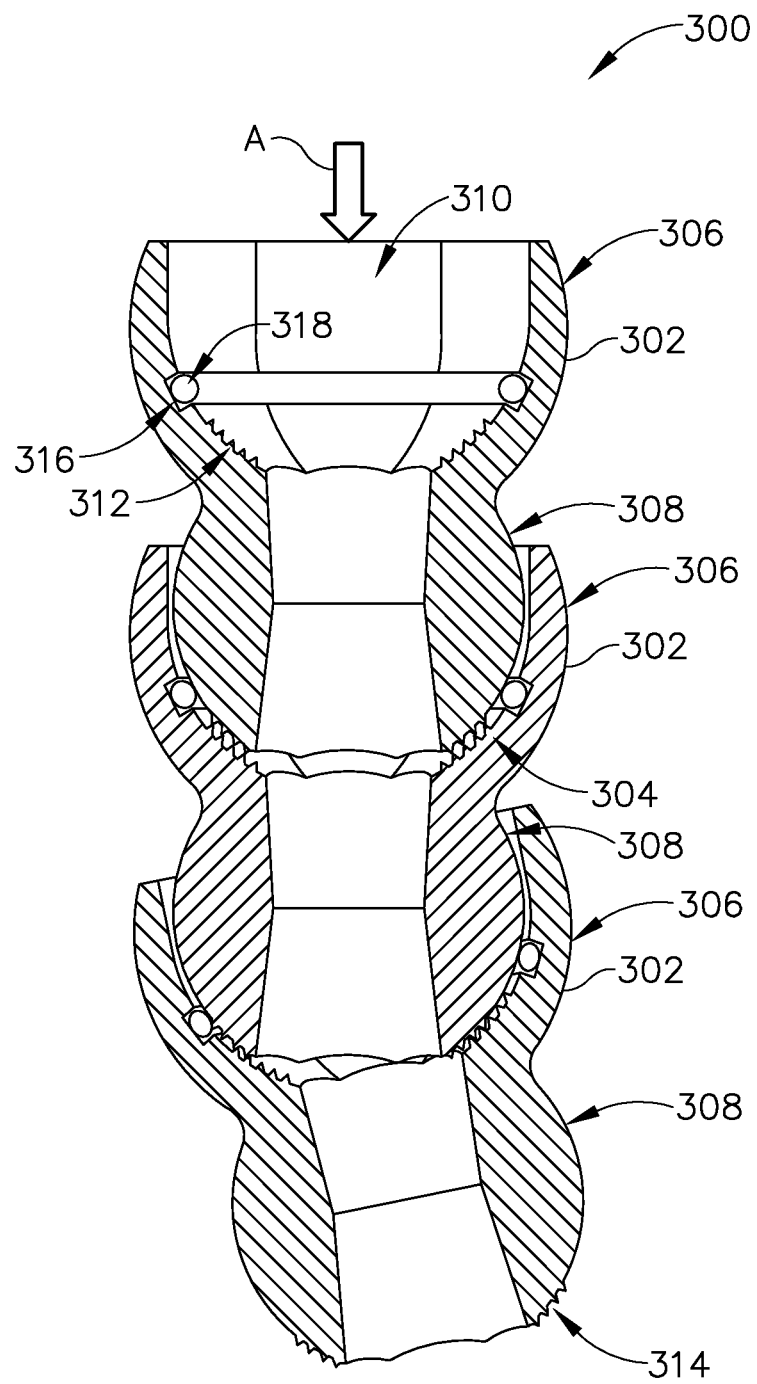
FIG. 8B depicts a cross-sectional elevation view of the shaft assembly of FIG. 8A in a second position.
Figure 10:
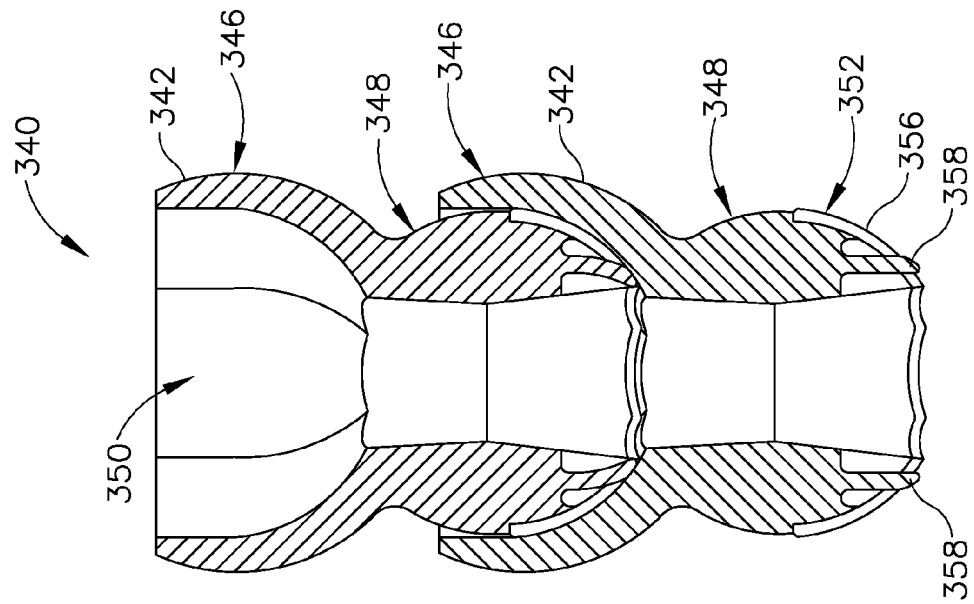
FIG. 10 depicts a cross-sectional elevation view of yet another exemplary shaft assembly that may be incorporated into the instrument of FIG. 7.
Figure 9:
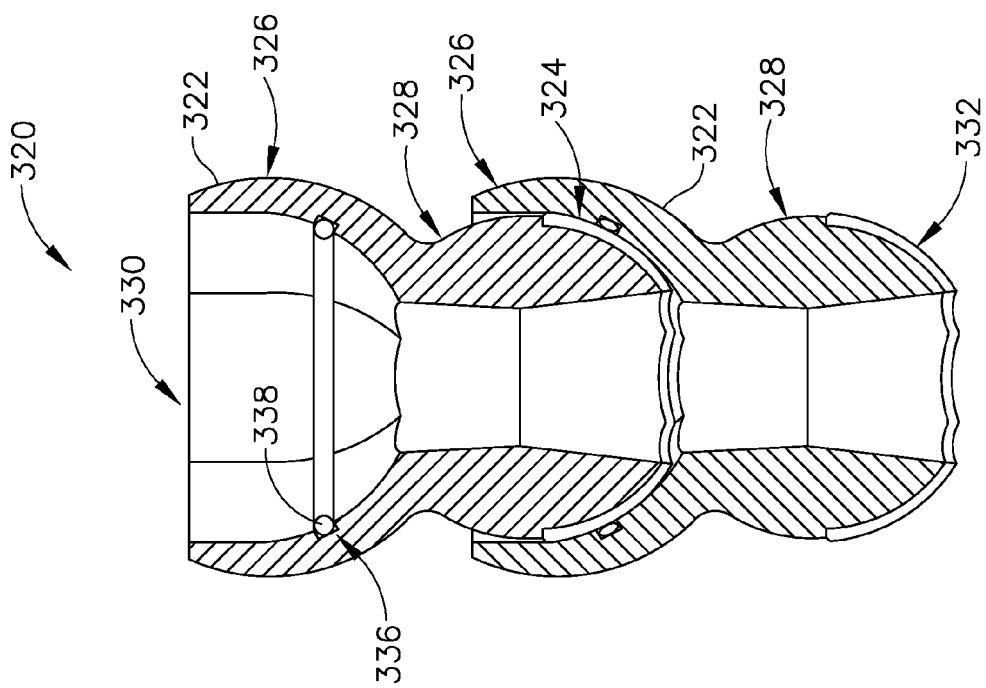
FIG. 9 depicts a cross-sectional elevation view of another exemplary shaft assembly that may be incorporated into the instrument of FIG. 7.

FIGS. 8-10 show versions of exemplary flexible sections of shaft assembly (260) in which flexible shaft joint segments are free to move against one another until locked against one another by a biasing, compressive force as described below.

FIGS. 8A and 8B show a first flexible section (300) that includes joint segments (302) that are inter-lockable via an o-ring and teeth assembly (304) to form a flexible, hollow drive tube that is selectively lockable as described below. Joint segments (302) and other versions of joint segments described below comprise plastic infilled or unfilled Nylon, Ultem, ABS, Polycarbonate or Polyethelene, for example, or other suitable material as will be apparent to those of ordinary skill in the art in view of the teachings herein. Joint segments (302) and other versions of joint segments described below may formed in accordance with at least some of the teachings of U.S. patent application Ser. No. 13/536,313, entitled "Rotary Drive Arrangements for Surgical Instruments," filed Jun. 28, 2012, the disclosure of which is incorporated by reference herein. Joint segments (302) each include a female distal portion (306) and a male proximal portion (308). Distal portion (306) includes interior wall surfaces that form a hexagonal or round cross-section. Proximal portion (308) includes an exterior surface with a respective hexagonal or round cross-section that is complementary with and sized and shaped to be received against the interior wall surfaces of distal portion (306). Channel (310) runs through distal portion (306) and proximal portion (308) and is defined by interior walls surfaces of both distal portion (306) and proximal portion (308). Channel (310) is sized and shaped to receive a tension cable in the direction of arrow (A) to, for example, lock joint segments (302) together in a compressed relationship as described below.

Interior wall surfaces of distal portion (306) of each joint segment (302) include teeth (312). An exterior wall surface of proximal portion (308) of each joint segment (302) includes teeth (314) that are sized and shaped to receive and mesh with teeth (312). Further, interior wall surfaces of distal portion (306) of each joint segment (302) include notch (316) and o-ring (318) disposed in notch (316).

In use, proximal portion (308) of a first joint segment (302) is received in distal portion (306) of a second joint segment (302). A tension cable (not shown) is fixed at a distal end of shaft assembly (260) and is received in channel (310). FIG. 8A shows an unlocked position in which proximal portion (308) of the first joint segment (302) is loosely received within distal portion (306) of the second joint segment (302) such that teeth (312, 314) are not meshed but are spaced apart and the first joint segment (302) is pivotable relative to the second joint segment (302). As the tension cable is not in tension in this unlocked position, the resilience of o-rings (318) drives teeth (314) out of engagement with teeth (312).

The tension cable may be retracted in the direction of arrow (A) to provide a compression force that compresses proximal portion (308) of the first joint segment (302) against distal portion (306) of the second joint segment (302). In particular, teeth (312) mesh with teeth (314) and an exterior wall surface of proximal portion (308) of the first joint segment (302) retracts against o-ring (318), causing o-ring (318) to compress within notch (316). Such compression and interlocking of teeth (312, 214) forms a locked series of joint segments (302) such that joint segments (302) no longer pivot relative to each other when teeth (312, 314) are locked together. In this locked position, flexible shaft section (263) will rigidly maintain a formed tortuous configuration. The locked flexible shaft section (263) also provides a rotational ground for stapling head assembly (220). A relief of tension in the tension cable will unlock joint segments (302) and would enable pivoting of joint segments (302) relative to one another as joint segments (302) would once more be in the unlocked position. While teeth (312, 314) are only shown in FIGS. 8A-8B, other joint segments described below may comprise similar interlocking teeth or ridge features.

FIG. 9 shows a second flexible section (320) that includes joint segments (322) that are inter-lockable via an o-ring and elastomeric ridge assembly (324). Joint segments (322) each include a female distal portion (326) and a male proximal portion (328). Distal portion (326) includes interior wall surfaces that form a hexagonal or round cross-section. Proximal portion (328) includes an exterior surface with a respective hexagonal or round cross-section that is complementary to and sized and shaped to be received against the interior wall surfaces of distal portion (326). Channel (330) runs through distal portion (326) and proximal portion (328) and is defined by interior walls surfaces of both distal portion (326) and proximal portion (328). Channel (330) is similar to channel (310) described above.

A lower exterior wall surface of proximal portion (328) includes a surrounding elastomeric ridge portion (332). Interior wall surfaces of distal portion (326) of each joint segment (322) include notch (336) and o-ring (338) disposed in notch (336).

In use, proximal portion (328) of a first joint segment (322) is received in distal portion (326) of a second joint segment (322). A tension cable (not shown) is received in channel (330) and may be retracted to provide a compression force that compresses proximal portion (328) of the first joint segment (322) against distal portion (326) of the second joint segment (322). In particular, elastomeric ridge portion (332) of proximal portion (328) of the first joint segment (322) compresses against o-ring (338), causing o-ring (338) to compress within notch (336). Elastomeric ridge portion (332) also compresses against the interior wall of distal portion (326). Without such compression, o-ring (338) biases proximal portion (328) of the first joint segment (322) away from receiving the interior wall of distal portion (326) of second segment (322) such that the first joint segment is pivotable with respect to the second joint segment. The compression otherwise provides significant friction that results in a locked series of joint segments (322).

FIG. 10 shows a second flexible section (340) that includes joint segments (342) that are inter-lockable via assembly (344). Joint segments (342) each include a female distal portion (346) and a male proximal portion (348). Distal portion (346) includes interior wall surfaces that form a hexagonal or round cross-section. Proximal portion (348) includes an exterior surface with a respective hexagonal or round cross-section that is complementary and sized and shaped to be received against the interior wall surfaces of distal portion (346). Channel (350) runs through distal portion (346) and proximal portion (348) and is defined by interior walls surfaces of both distal portion (346) and proximal portion (348). Channel (350) is similar to channel (310) described above.

A lower exterior wall surface of proximal portion (348) includes a surrounding resilient portion (352). Resilient portion (352) includes elastomeric ridge portion (356) and resilient prongs (358). In some other versions, resilient portion (352) includes a leaf spring and/or other resilient features (e.g., as a substitute for resilient prongs (358)).

In use, proximal portion (348) of a first joint segment (342) is received in distal portion (346) of a second joint segment (342). In an unlocked position, resilient prongs (358) bias the first joint segment (342) away from the second joint segment (342) substantially disengaging elastomeric ridge portion (356) such that the first joint segment (342) is pivotable with respect to the second joint segment (342). A tension cable (not shown) is received in channel (350) and may be retracted to provide a compression force that compresses proximal portion (348) of the first joint segment (342) against distal portion (346) of the second joint segment (342). In particular, resilient prongs (358) of the first joint segment (342) deform in response to the compression force. This retraction causes elastomeric ridge portion (356) to compress against the interior wall surfaces of distal portion (346) of the second joint segment (342), which provides friction that locks together segments (342) to form a locked series of joint segments (342).

B. Exemplary Rotary Drive Assemblies

Figure 12:
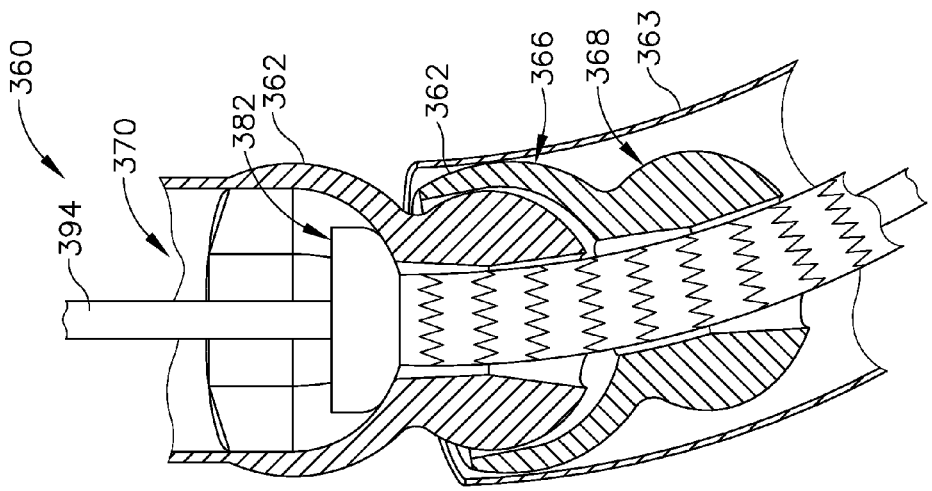
FIG. 12 depicts a cross-sectional elevation view of another exemplary rotary drive assembly that may be incorporated into the instrument of FIG. 7.
Figure 11:
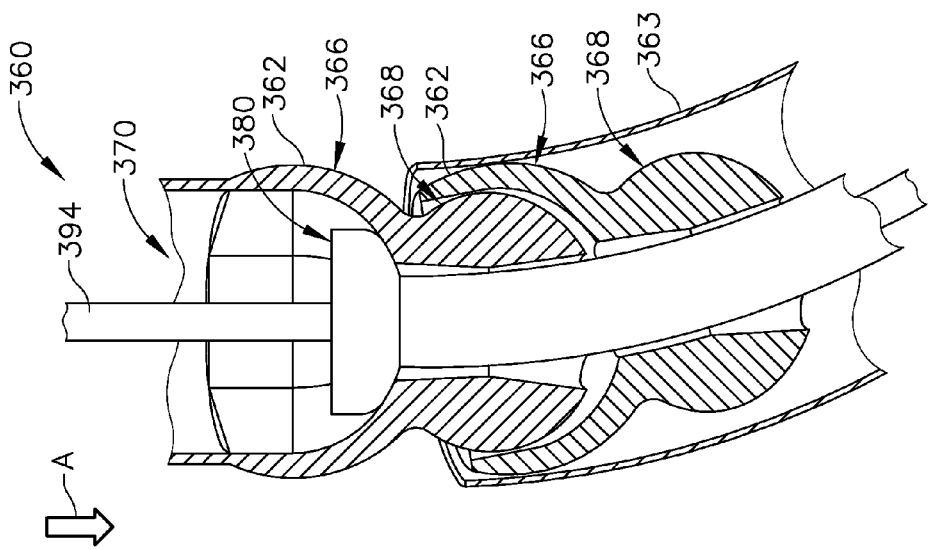
FIG. 11 depicts a cross-sectional elevation view of an exemplary rotary drive assembly that may be incorporated into the instrument of FIG. 7.
Figure 13:
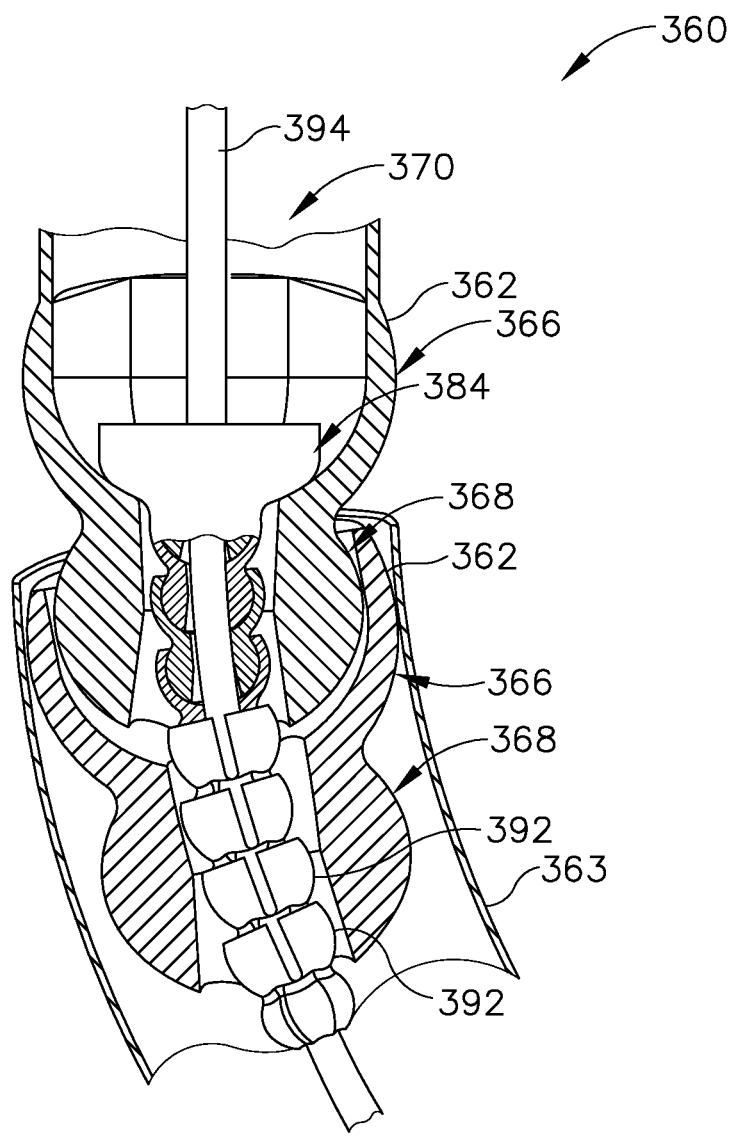
FIG. 13 depicts a cross-sectional elevation view of yet another exemplary rotary drive assembly that may be incorporated into the instrument of FIG. 7.

FIGS. 11-13 show a version of an exemplary flexible section (360) of shaft assembly (260) including three different versions of rotary drives. Exemplary flexible section (360) of shaft assembly (260) includes joint segments (362) that are inter-lockable via any manner as described above or as will be apparent to one of ordinary skill in the art in view of the teachings herein. Joint segments (362) are disposed in outer casing (363) to protect against tissue from being captured in areas between interlocking joint segments (362). Outer casing (363) may be outer tubular member (262) or may be a separate tube disposed in outer tubular member (262). Outer casing (363) is flexible in the present example.

Joint segments (362) each include a female distal portion (366) and a male proximal portion (368). Distal portion (366) includes interior wall surfaces that form a hexagonal or round cross-section. Proximal portion (368) includes an exterior surface with a respective hexagonal or round cross-section that is complementary to and sized and shaped to be received against the interior wall surfaces of distal portion (366). Channel (370) runs through distal portion (366) and proximal portion (368) and is defined by interior walls surfaces of both distal portion (366) and proximal portion (368). Channel (370) is similar to channel (310) described above.

A rotary drive shaft (380) is disposed in channel (370) and is operable to drive stapling head assembly (220) as described above. Rotary drive shaft (380) rotates based off of a single rotary input from handle assembly (270), namely motor (272). Stapling head assembly (220) is operable to clamp layers of tissue (2) between shaft assembly (260) and anvil (240), drive knife (36) to sever tissue, and drive staples (66) against anvil (240) to staple the tissue (2), all based off of the single rotary drive from rotary drive shaft (380). Rotary drive shaft (380) comprises a flexible polymer material forming either a solid or hollow shaft.

FIG. 11 show rotary drive shaft (380) that comprises a flexible sheath. FIG. 12 shows rotary drive shaft (382) that is similar to rotary drive shaft (380) except that rotary drive shaft (382) comprises a laser-cut tube. For example, rotary drive shaft (382) may comprise a hollow metal tube made of stainless steel, titanium, or any other suitable material as will be apparent to those of ordinary skill in the art in view of the teachings herein; and may form a series of joint segments. The joint segments of the tube comprise a plurality of interlocking dovetail and/or zig-zag shapes that are loosely interlocked and that are cut into the rotary drive shaft (382) via a laser. By way of example only, rotary drive shaft (382) may be constructed in accordance with at least some of the teachings of U.S. patent application Ser. No. 13/536,313, entitled "Rotary Drive Arrangements for Surgical Instruments," filed Jun. 28, 2012, published as U.S. Pat. Pub. No. 2014/0005678 on Jan. 2, 2014, the disclosure of which is incorporated by reference herein. Other suitable ways in which rotary drive shaft (382) may be constructed will be apparent to those of ordinary skill in the art in view of the teachings herein.

FIG. 13 shows rotary drive shaft (382) that comprises joint segments (392). Joint segments (392) are sized to be received within channels (310, 330, 350, 370) and are operable in any manner as described above for joint segments (302, 322, 342, 362) or in any other manner as will be apparent to one of ordinary skill in the art in view of the teachings herein.

Tension cable (394) is disposed in a lumen defined in rotary drive shaft (380, 382, 384). Tension cable (394) is operable to lock joint segments (302, 322, 342, 362) against one another in a manner as described above for joint segments (302, 322, 342, 362). Tension cable (394) may alternatively be disposed exterior to rotary drive shaft (380, 382, 384) and may include a lumen sized to receive rotary drive shaft (380, 382, 384).

C. Exemplary Locking Actuation Assemblies

Figure 14:
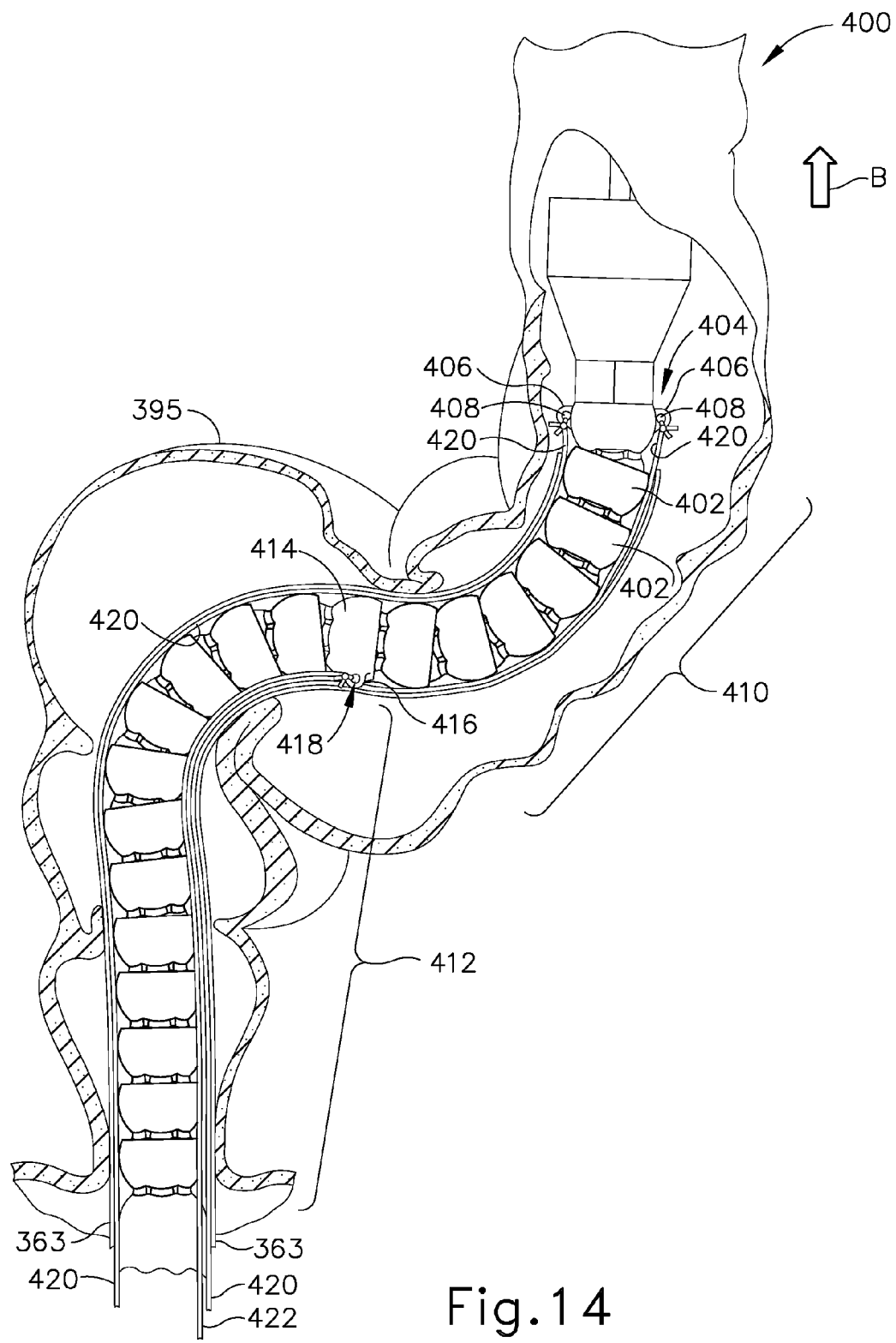
FIG. 14 depicts a cross-sectional elevation view of an exemplary locking actuator that may be incorporated into the instrument of FIG. 7.
Figure 15:
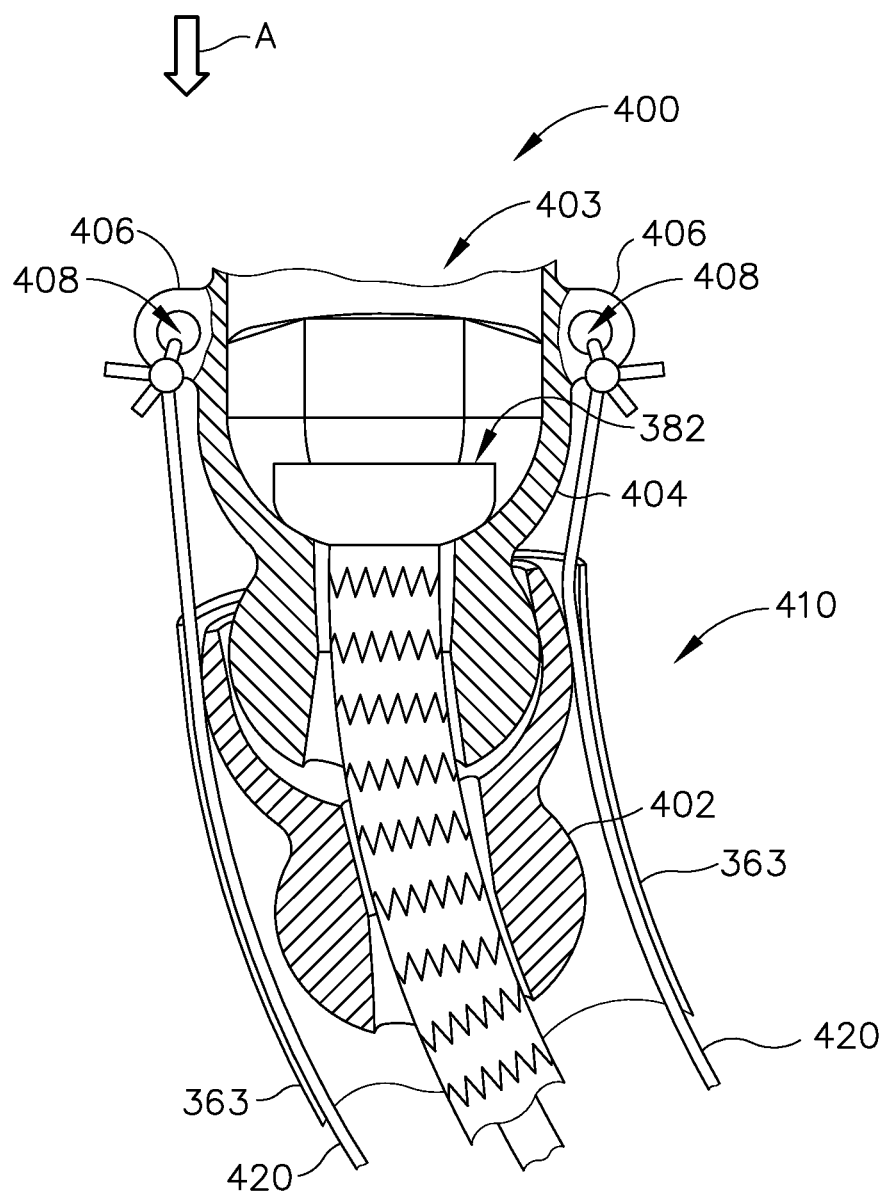
FIG. 15 depicts a fragmented cross-sectional view of a distal portion of the locking actuator of FIG. 14.
Figure 16:
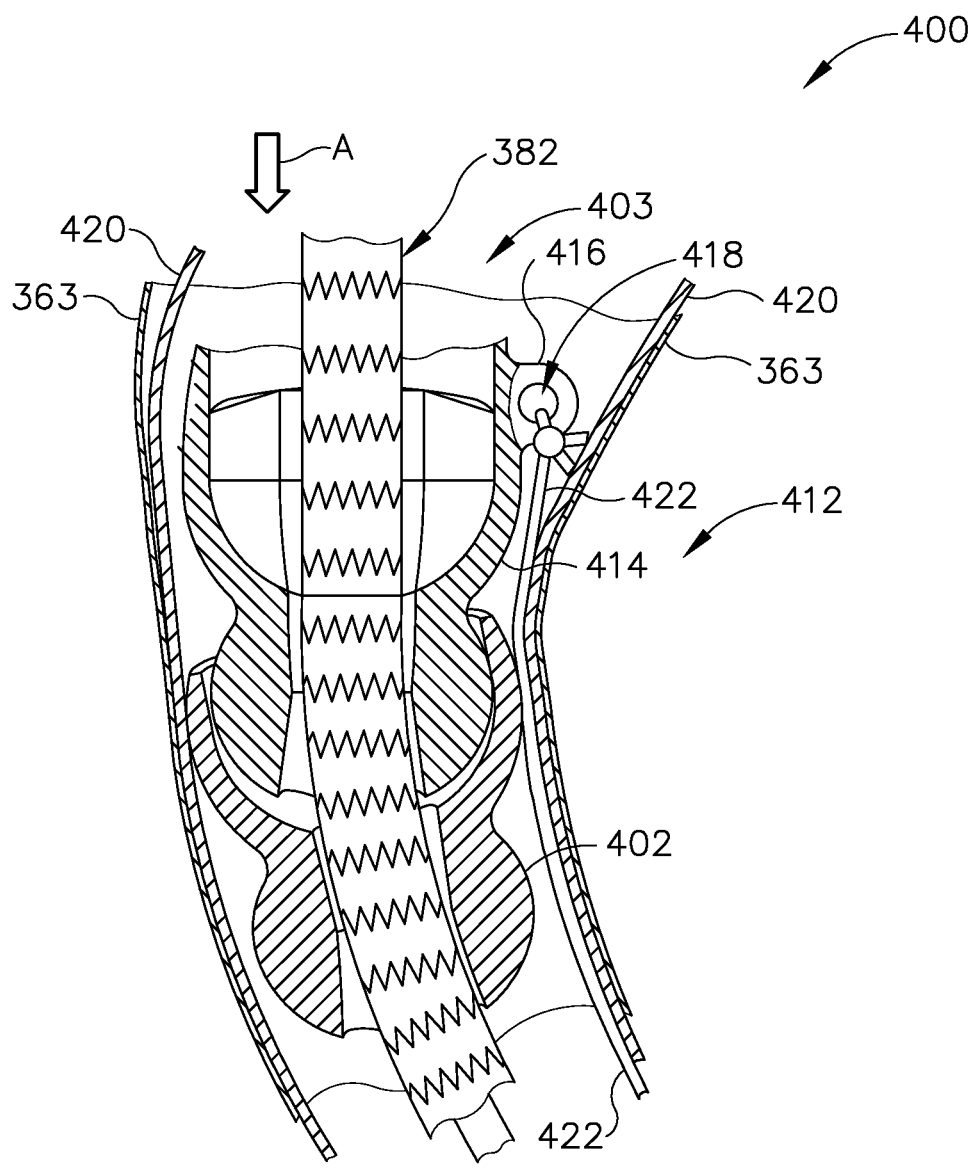
FIG. 16 depicts a fragmented cross-sectional view of a proximal portion of the locking actuator of FIG. 14.
Figure 17:
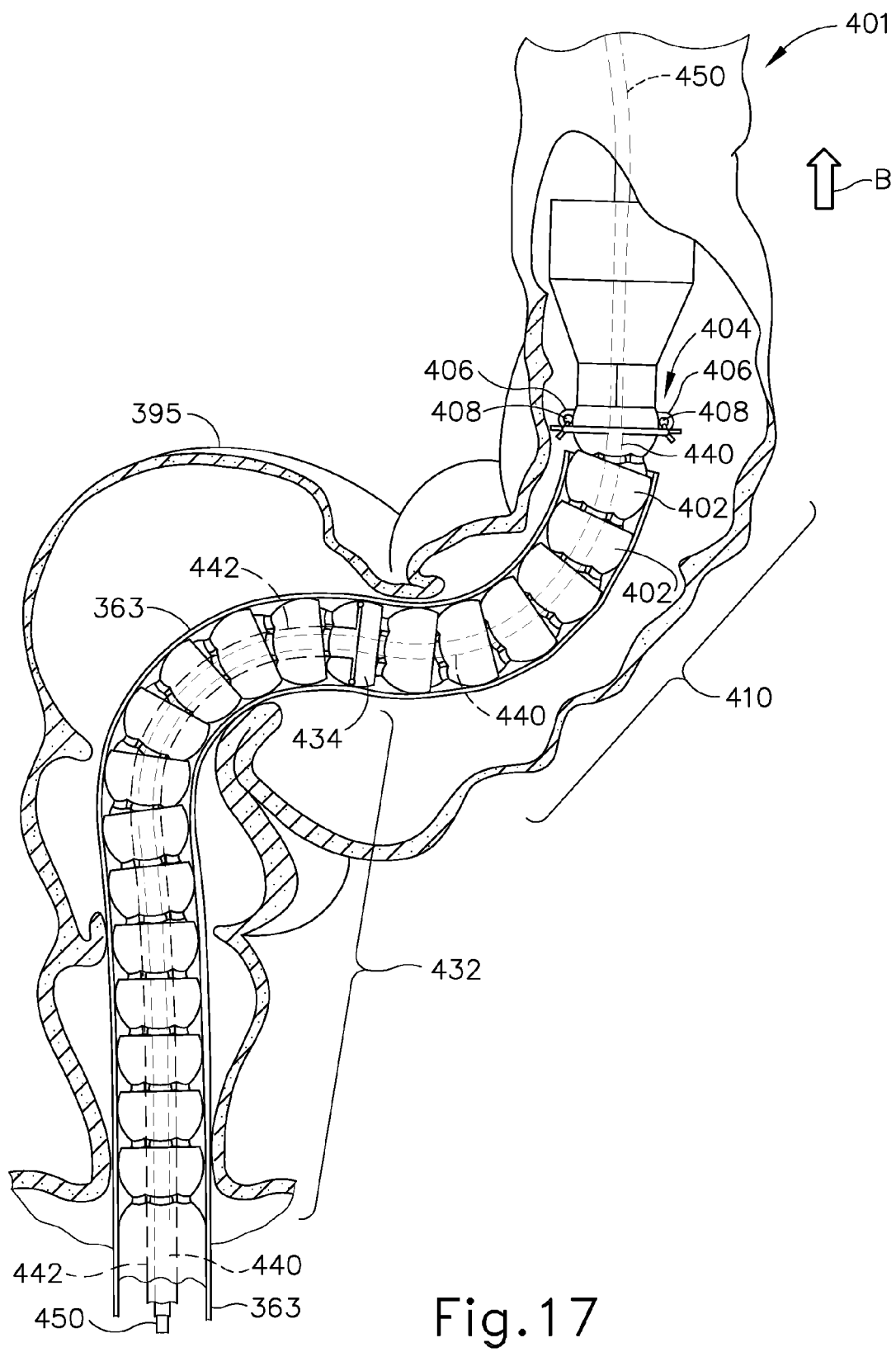
FIG. 17 depicts a cross-sectional elevation view of another exemplary locking actuator that may be incorporated into the instrument of FIG. 7.
Figure 18:
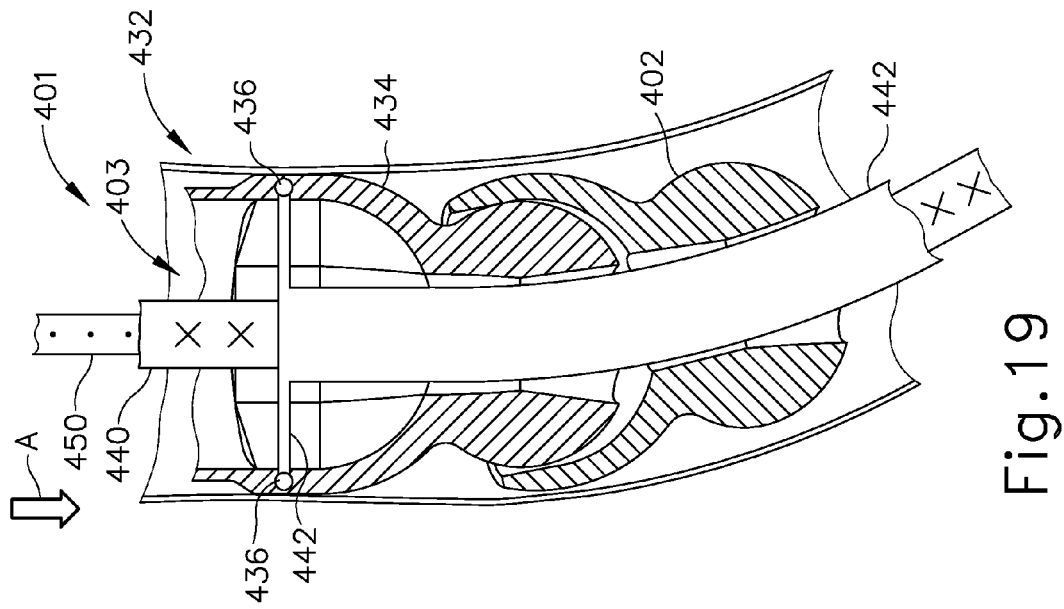
FIG. 18 depicts a fragmented cross-sectional view of a distal portion of the locking actuator of FIG. 17.
Figure 19:
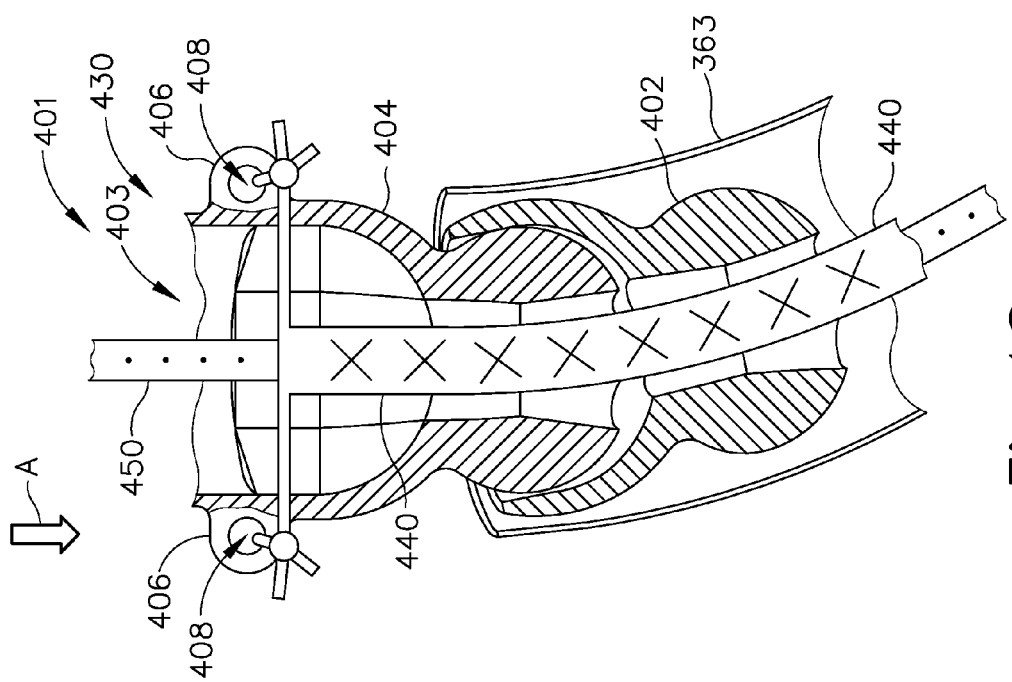
FIG. 19 depicts a fragmented cross-sectional view of a proximal portion of the locking actuator of FIG. 17.

FIGS. 14-16 show a first version of an exemplary locking actuator (400) and FIGS. 17-19 show a second version of an exemplary locking actuator (401). Both versions are shown in a colon (395) and both versions include some similar features such as interlocking joint segments (402) that are similar to joint segments (302, 322, 342, 362) of shaft assembly (260) described above and that are operable to distally advance shaft assembly (260) toward anvil (240) in the direction of arrow (B). Distal most joint segments (404) include a pair of projections (406) defining apertures (408). Both locking actuators (400, 401) include separate sections (410, 412, 430, 432) as described below and independent locking cables (420, 422) or independent locking shafts (440, 442) respectively associated with each separate section (410, 412, 430, 432) to allow for multiple articulation zones within shaft assembly (260) and to provide for a locking feature to prevent rotation of joint segments forming shaft assembly (260) as described above.

FIG. 14 shows a distal locking segment section (410) and a proximal locking segment section (412) of locking actuator (400). Distal locking segment section (410) and proximal locking segment section (412) may be selectively locked independently relative to each other. Distal-most joint segment (404) is disposed at a distal end of distal locking segment section (410). A distal most joint segment (414) of proximal locking segment section (412) includes a single projection (416) that defines aperture (418).

Each of a pair of outer locking cables (420) is disposed between outer casing (363) and joint segments (402). A distal end of each outer locking cable (420) is attached to a respective projection (406). Outer locking cables (420) are received within apertures (408) and tied about projections (406). Outer locking cables (420) may be attached to projections (408) or distal most joint segment (404) of distal locking segment section (410) in any suitable manner as will be apparent to those of ordinary skill in the art in view of the teachings herein.

An inner locking cable (422) is disposed adjacent to one outer locking cable (420) and joint segments (402). By way of example only, the pair of outer locking cables (420) and inner locking cable (422) may be positioned at the same radial distance and be angularly offset from each other. A distal end of inner locking cable (422) is attached to projection (416). The distal end of inner locking cable (422) is received within aperture (418) and tied about projection (416). Inner locking cable (422) may be attached to projection (418) or distal most joint segment (414) of proximal locking segment (412) in any suitable manner as will be apparent to those of ordinary skill in the art in view of the teachings herein.

When at least one set of cables (420, 422) are in a loose and unlocked position, and/or when cables (420, 422) are released (e.g., distally advanced), the unlocked cables (420, 422) allow associated joint segments (402) to pivot relative to one another. When at least one set of cables (420, 422) are retracted proximally, joint segments (402) are rigidly locked to one another. One of proximal locking segment section (412) and distal locking segment section (410) may be locked while the other of proximal locking segment section (412) and distal locking segment section (410) is loose. For example, proximal locking segment section (412) may be locked into place while distal locking segment section (410) is loose to provide support for moving through difficult and/or narrow passages of colon (395). Once in place, both distal locking segment section (410) and proximal locking segment section (412) may be in preparation for firing shaft assembly (260) against anvil (240) as described above. Each of proximal locking segment section (412) and distal locking segment section (410) may have any suitable number of cables as will be apparent to those of ordinary skill in the art in view of the teachings herein.

FIGS. 15-16 show rotary drive shaft (382) disposed in channel (403) extending through joint segments (402, 404, 414). Other suitable rotary drive shafts as will be apparent to those of skill in the art in view of the teachings herein, such as those rotary drive shafts described above, are alternatively disposable within channel (403).

In use, outer locking cables (420) provide a force in the direction of arrow (A) to compress joint segments (402, 404) of distal locking segment section (410) against one another. Inner locking cable (422) provides a force in the direction of arrow (A) to compress joint segments (402, 414) of proximal locking segment section (412) against one another such that proximal locking segment section (412) and distal locking segment section (410) are independently compressible and lockable such that joint segments (402, 404, 414) do not rotate against one another in a locked position.

FIG. 17 shows a distal locking segment section (430) and a proximal locking segment section (432) of locking actuator (400). Distal locking segment section (430) and proximal locking segment section (432) may be selectively locked independently relative to each other. Distal-most joint segment (404) is disposed at a distal end of distal locking segment section (430). A distal most joint segment (434) of proximal locking segment section (432) includes apertures (436) defined in a wall surface of distal most joint segment (434).

Inner locking shaft (440) is disposed within channel (403) extending through joint segments (402, 404, 435). A distal end of inner locking shaft (440) is attached to projections (406). End portions of the distal end of inner locking shaft (440) are respectively received within apertures (408) and tied about projections (406). Inner locking shaft (440) may be attached to projections (408) or distal most joint segment (404) of distal locking segment section (430) in any suitable manner as will be apparent to those of ordinary skill in the art in view of the teachings herein.

An outer locking shaft (442) is disposed between inner locking shaft (440) and wall surfaces of channel (403) of joint segments (402, 434). A distal end of outer locking shaft (442) is attached to apertures (436). Portions of the distal end of outer locking shaft (442) are received within apertures (438). Outer locking shaft (442) may be attached to distal most joint segment (434) of proximal locking segment (432) in any suitable manner as will be apparent to those of ordinary skill in the art in view of the teachings herein.

When at least one shaft (440, 442) is in a loose and unlocked position, and/or when shafts (440, 442) are released (e.g., distally advanced), the unlocked shafts (440, 442) allow associated joint segments (402) to pivot relative to one another. Thus, in the unlocked position, joint segments (402) are able to travel along a tortuous path formed by a tortuous section of a lumen of tissue (for example, to reach the transverse colon via insertion through the rectum). When at least one set of shafts (440, 442) are retracted proximally, the corresponding joint segments (402) are rigidly locked to one another. In the locked position, joint segments (402) are rigidly locked together to prepare for the actuation of stapling head assembly (220) and provide a mechanical ground for this actuation. Release of shafts (440, 442) allow joint segments (402) to unlock and pivot relative to one another such that flexible section (263) may be flexibly retracted along the tortuous path. One of proximal locking segment section (432) and distal locking segment section (430) may be locked while the other of proximal locking segment section (432) and distal locking segment section (430) is loose. For example, proximal locking segment section (432) may be locked into place while distal locking segment section (430) is loose to provide support for moving through difficult and/or narrow passages of colon (395). Once in place, both distal locking segment section (430) and proximal locking segment section (432) may be in preparation for firing shaft assembly (260) against anvil (240) as described above.

FIGS. 18-19 show rotary drive cable (450) disposed in channel (403) extending through joint segments (402, 404, 434). Rotary drive cable (450) may be similar to any of the rotary drive shafts as described above or as will be apparent to those of skill in the art in view of the teachings herein.

In use, inner locking shaft (440) provides a force in the direction of arrow (A) to compress joint segments (402, 404) of distal locking segment section (430) against one another. Outer locking shaft (442) provides a force in the direction of arrow (A) to compress joint segments (402, 434) of proximal locking segment section (432) against one another such that proximal locking segment section (432) and distal locking segment section (430) are independently compressible and lockable such that joint segments (402, 404, 434) do not pivot relative to one another in a locked configuration.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep.

14, 2010, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/693,430, entitled "Trans-Oral Circular Anvil Introduction System with Dilation Feature," filed Dec. 4, 2012, now U.S. Pat. No. 9,199,232, issued Dec. 1, 2015, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/688,951, entitled "Surgical Staple with Integral Pledget for Tip Deflection," filed Nov. 29, 2012, and published as U.S. Pat. Pub. No. 2014/0144963 on May 29, 2014, now U.S. Pat. No. 9,289,207, issued Mar. 22, 2016, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/706,827, entitled "Surgical Stapler with Varying Staple Widths Along Different Circumferences," filed Dec. 6, 2012, and published as U.S. Pat. Pub. No. 2014/0158747 on Jun. 12, 2014, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/688,992, entitled "Pivoting Anvil for Surgical Circular Stapler," filed Nov. 29, 2012, and published as U.S. Pat. Pub. No. 2014/0144969 on May 29, 2014, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/693,455, entitled "Circular Anvil Introduction System with Alignment Feature," filed Dec. 4, 2012, and published as U.S. Pat. Pub. No. 2014/0151430 on Jun. 5, 2014, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/716,308, entitled "Circular Stapler with Selectable Motorized and Manual Control," filed on Dec. 17, 2012, and published as U.S. Pat. Pub. No. 2014/0166727 on Jun. 19, 2014, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/716,313, entitled "Circular Stapler with Selectable Motorized and Manual Control, Including a Control Ring," filed on Dec. 12, 2012, and published as U.S. Pat. Pub. No. 2014/0166717 on Jun. 19, 2014, the disclosure of which is incorporated by reference herein. Various suitable ways in which such teachings may be combined will be apparent to those of ordinary skill in the art.

Similarly, at least some of the teachings herein may be readily combined with one or more teachings of U.S. patent application Ser. No. 13/716,318, entitled "Motor Driven Rotary Input Circular Stapler with Modular End Effector," filed on Dec. 17, 2012, and published as U.S. Pat. Pub. No. 2014/0166728 on Jun. 19, 2014, the disclosure of which is incorporated by reference herein. Various suitable ways in which such teachings may be combined will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A circular stapler apparatus for stapling tissue, the apparatus comprising:
   (a) a staple head assembly operable to drive staples into tissue;
   (b) a shaft assembly, the shaft assembly comprising:
      (i) a plurality of joint segments, wherein each joint segment includes a male coupling portion and a female coupling portion, and wherein each female coupling portion is configured to receive the male coupling portion, wherein the plurality of joint segments are configured to pivot relative to one another in a first, uncompressed position and are configured to lock against one another to prevent pivoting in a second, compressed position, and
      (ii) a plurality of resilient members positioned respectively between the plurality of male coupling portions and the plurality of female coupling portions, wherein each resilient member is configured to bias and space the respective male coupling portion away from the respective female coupling portion to the first, uncompressed position for disengaging the plurality of joint segments from each other; and
   (c) an anvil configured to proximally retract toward the shaft assembly, wherein the shaft assembly and anvil together are configured to at least sever or staple tissue based on a single rotary input.

2. The apparatus of claim 1, wherein each joint segment includes a distal portion and a proximal portion, wherein the distal portion comprises a wall surface having a hexagonal cross-sectional shape, wherein the proximal portion comprises a wall surface having a hexagonal cross-sectional shape, wherein the distal portion of a first joint segment includes the female coupling portion and the proximal portion of a second joint segment includes the male coupling portion such that female coupling portion of the first joint segment is configured to receive the male coupling portion of the second joint segment.

3. The apparatus of claim 2, wherein each segment comprises teeth in the interior wall surface of the distal portion and teeth on the exterior wall surface of the proximal portion.

4. The apparatus of claim 3, wherein the teeth in the interior wall surface of the distal portion of the first segment are configured to mesh with the teeth on the exterior wall surface of the proximal portion of the second segment.

5. The apparatus of claim 4, wherein the interior wall surface of each distal portion comprises a notch and an o-ring, wherein the o-ring is disposed in the notch above the teeth in the interior wall surface of the distal portion, wherein the o-ring is configured to compress to provide a compressive force against the meshed teeth of the first segment and the second segment.

6. The apparatus of claim 2, wherein the interior wall surface of each distal portion comprises a notch and an o-ring, wherein the o-ring is configured to compress against a compressive force applied in response to the retraction of the second joint segment toward the first joint segment to lock the second joint segment to the first joint segment.

7. The apparatus of claim 6, wherein the proximal portion of each joint segment comprises an elastomeric ridge portion, wherein the elastomeric ridge portion of the first joint segment is configured to compress the o-ring of the second joint segment.

8. The apparatus of claim 2, wherein each of the resilient members of the second joint segment is configured to compress against the hexagonal wall surface of the first joint segment.

9. The apparatus of claim 2, wherein the plurality of joint segments comprise a channel, wherein the channel is configured to receive a tension cable operable to provide a compressive force in a first direction to lock the first joint segment against the second joint segment.

10. The apparatus of claim 9, wherein the channel is configured to receive a rotary drive shaft operable to drive the staple head assembly, wherein the rotary drive shaft is configured to receive the tension cable.

11. The apparatus of claim 10, further comprising an outer casing disposed around the plurality of joint segments, and wherein the rotary drive shaft comprises a flexible tube.

12. The apparatus of claim 10, wherein the rotary drive shaft comprises a plurality of joint segments, wherein the plurality of joint segments of the rotary drive shaft are configured to pivot relative to one another.

13. The apparatus of claim 2, wherein a first plurality of joint segments define a proximal segmented portion and a second plurality of joint segments define a distal segmented portion, wherein the proximal segmented portion is selectively lockable independent of the distal segmented portion.

14. The apparatus of claim 13, wherein a first cable is attached to the proximal segmented portion, wherein a second cable is attached to the second segmented portion, and wherein each joint segment of the plurality of joint segments are configured to pivot relative to one another in a first, uncompressed position and are configured to lock against one another to prevent pivoting in a second, compressed position.

15. A circular stapler apparatus for stapling tissue, the apparatus comprising:
   (a) a staple head assembly operable to drive staples into tissue;
   (b) a shaft assembly, the shaft assembly comprising:
      (i) a first plurality of joint segments defining a proximal segmented portion and a second plurality of joint segments defining a distal segmented portion, wherein the first plurality of joint segments and the second plurality of joint segments define a channel, wherein the proximal segmented portion is selectively lockable independent of the distal segmented portion, wherein a first member is attached to the proximal segmented portion, wherein a second member is attached to the distal segmented portion, and wherein the plurality of joint segments are configured to pivot relative to one another in a first, uncompressed position and are configured to lock against one another to prevent pivoting in a second, compressed position, wherein the first member is configured to retract to place the joint segments of the distal segmented portion into the second, compressed position, and wherein the second member is configured to independently retract to place the joint segments of the proximal segmented portion into the second, compressed position; and (c) an anvil configured to proximally retract toward the shaft assembly, wherein the shaft assembly and anvil together are configured to at least sever or staple tissue based on a single rotary input.

16. The apparatus of claim 15, wherein the first and second members respectively comprise first and second cables.

17. The apparatus of claim 15, wherein the first member comprises an outer shaft, wherein the outer shaft is disposed in the channel, wherein the second member comprises an inner shaft, and wherein the inner shaft is disposed in the outer shaft.

18. A circular stapler apparatus for stapling tissue, the apparatus comprising:
(a) a staple head assembly operable to drive staples into tissue;
(b) a shaft assembly, the shaft assembly comprising:
   (i) a plurality of joint segments, wherein each joint segment includes a male coupling portion and a female coupling portion, and wherein each female coupling portion is configured to receive the corresponding male coupling portion, wherein the plurality of joint segments are configured to pivot relative to one another in a first, uncompressed position and are configured to lock against one another to prevent pivoting in a second, compressed position, and
   (ii) a plurality of resilient members positioned respectively between the plurality male coupling portions and the female coupling portions, wherein each resilient member is configured to bias and space the respective male coupling portion away from the respective female coupling portion to the first, uncompressed position for disengaging the plurality of joint segments from each other; and
(c) an anvil configured to proximally retract toward the shaft assembly, wherein the shaft assembly and anvil together are configured to at least sever or staple tissue based on a single rotary input; and
(d) a rotary drive shaft operable to drive the staple head assembly in response to the single rotary input.

19. The apparatus of claim 1, wherein the male coupling portion includes a plurality of teeth extending therefrom, and wherein the plurality of teeth are configured to engage the female coupling portion and lock theregainst in the second, compressed position.

20. The apparatus of claim 1, wherein the plurality of resilient members includes an o-ring, wherein the female coupling portion includes a notch, wherein the o-ring is received within the notch, wherein the o-ring is configured to be compressed by the male coupling portion received thereagainst in response to the retraction at least one of the male coupling portions toward at least one of the female coupling portions in the second, compressed position for locking the plurality of joint segments, respectively.

21. The apparatus of claim 1, wherein the plurality of resilient members includes a pair of resilient prongs proximally extending from the male coupling portion, wherein the male coupling portion includes a proximal end and the pair of resilient prongs are configured to extend proximally past the proximal end in first, uncompressed position, and wherein the pair of resilient prongs are configured to compress against the female coupling portion in the second, compressed position for locking the plurality of joint segments.

\* \* \* \* \*